(12) United States Patent
Zehner et al.

(10) Patent No.: US 6,881,205 B2
(45) Date of Patent: Apr. 19, 2005

(54) INDEPENDENCE OF COMPONENTS IN ABSORBENT ARTICLES

(75) Inventors: Georgia Lynn Zehner, Larsen, WI (US); John Philip Vukos, Neenah, WI (US); Duane Girard Uitenbroek, Little Chute, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/011,087

(22) Filed: Dec. 7, 2001

(65) Prior Publication Data

US 2002/0052590 A1 May 2, 2002

Related U.S. Application Data

(63) Continuation-in-part of application No. 09/698,517, filed on Oct. 27, 2000.

(51) Int. Cl.[7] .............................................. A61F 13/15
(52) U.S. Cl. ........................ 604/385.01; 604/385.23; 604/385.16
(58) Field of Search ..................... 604/385.01, 385.16, 604/385.22, 385.23, 378, 385.25, 385.26, 396, 385.3

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,538 A | 3/1970 | Peterson | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 4,340,563 A | 7/1982 | Appel et al. | |

(Continued)

FOREIGN PATENT DOCUMENTS

| | | | | |
|---|---|---|---|---|
| EP | 321 985 | 6/1989 | | |
| EP | 236 032 | 12/1991 | | |
| EP | 386 816 | 4/1994 | | |
| EP | 591 647 | 4/1994 | | |
| EP | 400 111 | 8/1994 | | |
| EP | 451 705 | 8/1994 | | |
| EP | 630 630 | * 12/1994 | | |
| EP | 630 631 | * 12/1994 | | |
| EP | 630 632 | * 12/1994 | | |
| EP | 420 256 | 5/1995 | | |
| EP | 706 106 | 4/1996 | | |
| EP | 433 951 | 8/1996 | | |
| EP | 522 345 | 9/1996 | | |
| EP | 630 221 | 4/1997 | | |
| EP | 409 315 | 5/1997 | | |
| EP | 820 747 | 1/1998 | | |
| EP | 602 613 | 6/1998 | | |
| EP | 651 629 | * 6/1998 | | |
| EP | 659 117 | * 6/1998 | | |
| WO | 93/01785 | 2/1993 | | |
| WO | 93/17648 | 9/1993 | | |
| WO | 94/02094 | 2/1994 | | |
| WO | WO 95/07063 | 3/1995 | | |
| WO | 96/16625 | 6/1996 | | |
| WO | 96/18367 | 6/1996 | | |
| WO | 97/36566 | 10/1997 | | |
| WO | WO 98/55065 | 12/1998 | | |
| WO | WO 9933426 A1 | * 7/1999 | ........... | A61F/13/15 |
| WO | WO 99/59514 | 11/1999 | | |
| WO | 00/30582 | 6/2000 | | |

*Primary Examiner*—Jacqueline Stephens
(74) *Attorney, Agent, or Firm*—Pauley Petersen & Erickson

(57) ABSTRACT

An absorbent article which minimizes or avoid component bonding within the interior area thereof is provided to improve or increase the independence of the components which constitute the article.

45 Claims, 20 Drawing Sheets

U.S. PATENT DOCUMENTS

| | | | |
|---|---|---|---|
| 4,443,513 A | | 4/1984 | Meitner et al. |
| 4,543,099 A | | 9/1985 | Bunnelle et al. |
| 4,606,964 A | | 8/1986 | Wideman |
| 4,640,726 A | | 2/1987 | Sallee et al. |
| 4,687,477 A | | 8/1987 | Suzuki et al. |
| 4,695,278 A | | 9/1987 | Lawson |
| 4,704,116 A | | 11/1987 | Enloe |
| 4,720,415 A | * | 1/1988 | Vander Wielen et al. |
| 4,756,709 A | * | 7/1988 | Stevens |
| 4,801,485 A | * | 1/1989 | Sallee et al. |
| 4,810,556 A | | 3/1989 | Kobayashi et al. |
| 4,829,096 A | | 5/1989 | Kitamura et al. |
| 4,838,885 A | | 6/1989 | Bernardin |
| 4,863,779 A | * | 9/1989 | Daponte |
| 4,891,258 A | | 1/1990 | Fahrenkrug |
| 4,908,247 A | * | 3/1990 | Baird et al. |
| 4,938,757 A | | 7/1990 | Van Gompel et al. |
| 4,965,122 A | | 10/1990 | Morman |
| 4,981,747 A | | 1/1991 | Morman |
| 5,036,551 A | | 8/1991 | Dailey et al. |
| 5,087,255 A | | 2/1992 | Sims |
| 5,114,781 A | | 5/1992 | Morman |
| 5,116,662 A | | 5/1992 | Morman |
| 5,143,679 A | * | 9/1992 | Weber et al. |
| 5,156,793 A | * | 10/1992 | Buell et al. |
| 5,167,897 A | * | 12/1992 | Weber et al. |
| 5,171,239 A | | 12/1992 | Igaue et al. |
| 5,171,388 A | * | 12/1992 | Hoffman et al. |
| 5,244,482 A | | 9/1993 | Hassenboehler, Jr. et al. |
| 5,259,902 A | * | 11/1993 | Muckenfuhs |
| 5,296,289 A | | 3/1994 | Collins |
| 5,322,728 A | | 6/1994 | Davey et al. |
| 5,336,545 A | | 8/1994 | Morman |
| 5,354,400 A | | 10/1994 | Lavash et al. |
| 5,370,632 A | | 12/1994 | Beplate |
| 5,374,259 A | | 12/1994 | Takahashi et al. |
| 5,385,775 A | | 1/1995 | Wright |
| 5,397,316 A | | 3/1995 | LaVon et al. |
| 5,464,401 A | | 11/1995 | Hasse et al. |
| 5,470,640 A | | 11/1995 | Modrak |
| 5,492,753 A | | 2/1996 | Levy et al. |
| 5,496,429 A | | 3/1996 | Hasse et al. |
| 5,514,470 A | | 5/1996 | Haffner et al. |
| 5,527,302 A | | 6/1996 | Endres et al. |
| 5,531,727 A | | 7/1996 | Cohen et al. |
| 5,554,143 A | | 9/1996 | Roe et al. |
| 5,554,144 A | | 9/1996 | Roe et al. |
| 5,554,145 A | | 9/1996 | Roe et al. |
| 5,556,392 A | | 9/1996 | Koczab |
| 5,556,394 A | | 9/1996 | Roe et al. |
| 5,556,504 A | | 9/1996 | Rajala et al. |
| 5,560,878 A | | 10/1996 | Dragoo et al. |
| 5,562,650 A | * | 10/1996 | Everett et al. .............. 604/378 |
| 5,569,232 A | | 10/1996 | Roe et al. |
| 5,569,234 A | | 10/1996 | Buell et al. |
| 5,582,903 A | | 12/1996 | Levy et al. |
| 5,587,225 A | | 12/1996 | Griesbach et al. |
| 5,591,151 A | | 1/1997 | Hasse et al. |
| 5,611,790 A | | 3/1997 | Osborn, III et al. |
| 5,615,460 A | | 4/1997 | Weirich et al. |
| 5,624,422 A | | 4/1997 | Allen |
| 5,624,427 A | | 4/1997 | Bergman et al. |
| 5,624,729 A | | 4/1997 | Cohen et al. |
| 5,628,741 A | | 5/1997 | Buell et al. |
| 5,628,856 A | | 5/1997 | Dobrin et al. |
| 5,635,290 A | | 6/1997 | Stopper et al. |
| 5,643,396 A | | 7/1997 | Rajala et al. |
| 5,645,672 A | | 7/1997 | Dobrin |
| 5,652,051 A | | 7/1997 | Shawver et al. |
| 5,658,269 A | | 8/1997 | Osborn, III et al. |
| 5,660,657 A | | 8/1997 | Rajala et al. |
| 5,674,212 A | | 10/1997 | Osborn, III et al. |
| 5,683,375 A | | 11/1997 | Osborn, III et al. |
| 5,690,626 A | | 11/1997 | Suzuki et al. |
| 5,690,627 A | | 11/1997 | Clear et al. |
| 5,702,382 A | | 12/1997 | Osborn, III et al. |
| 5,713,884 A | | 2/1998 | Osborn, III et al. |
| 5,716,478 A | | 2/1998 | Boothe et al. |
| 5,749,866 A | | 5/1998 | Roe et al. |
| 5,749,989 A | | 5/1998 | Linman et al. |
| 5,759,340 A | | 6/1998 | Boothe et al. |
| 5,797,895 A | | 8/1998 | Widlund et al. |
| H1750 H | | 9/1998 | Dobrin |
| 5,820,620 A | | 10/1998 | Allison-Rogers |
| 5,843,056 A | | 12/1998 | Good et al. |
| 5,882,769 A | | 3/1999 | McCormack et al. |
| 5,883,028 A | | 3/1999 | Morman et al. |
| 5,916,663 A | | 6/1999 | Chappell et al. |
| 5,921,973 A | | 7/1999 | Newkirk et al. |
| 5,942,569 A | | 8/1999 | Simmons et al. |
| 5,964,743 A | | 10/1999 | Abuto et al. |
| 5,993,431 A | | 11/1999 | McFall et al. |
| 5,997,989 A | | 12/1999 | Gessner et al. |
| 6,004,306 A | | 12/1999 | Robles et al. |
| 6,022,338 A | | 2/2000 | Putzer |
| 6,049,023 A | | 4/2000 | Blenke et al. |
| 6,056,733 A | | 5/2000 | Kielpikowski |
| 6,075,178 A | * | 6/2000 | La Wilhelm et al. ....... 604/361 |
| 6,102,892 A | | 8/2000 | Putzer et al. |
| 6,127,594 A | | 10/2000 | Rosseland |
| 6,129,720 A | | 10/2000 | Blenke et al. |
| 6,132,410 A | | 10/2000 | Van Gompel et al. |
| 6,152,907 A | | 11/2000 | Widlund et al. |
| 6,156,020 A | | 12/2000 | Roe et al. |
| 6,156,023 A | | 12/2000 | Yoshioka |
| 6,166,285 A | | 12/2000 | Schulte et al. |
| 6,171,290 B1 | | 1/2001 | Boisse et al. |
| 6,174,303 B1 | | 1/2001 | Suprise et al. |
| 6,197,404 B1 | | 3/2001 | Varona |
| 6,203,654 B1 | | 3/2001 | McFall et al. |
| 6,479,154 B1 | | 11/2002 | Walton et al. |

* cited by examiner

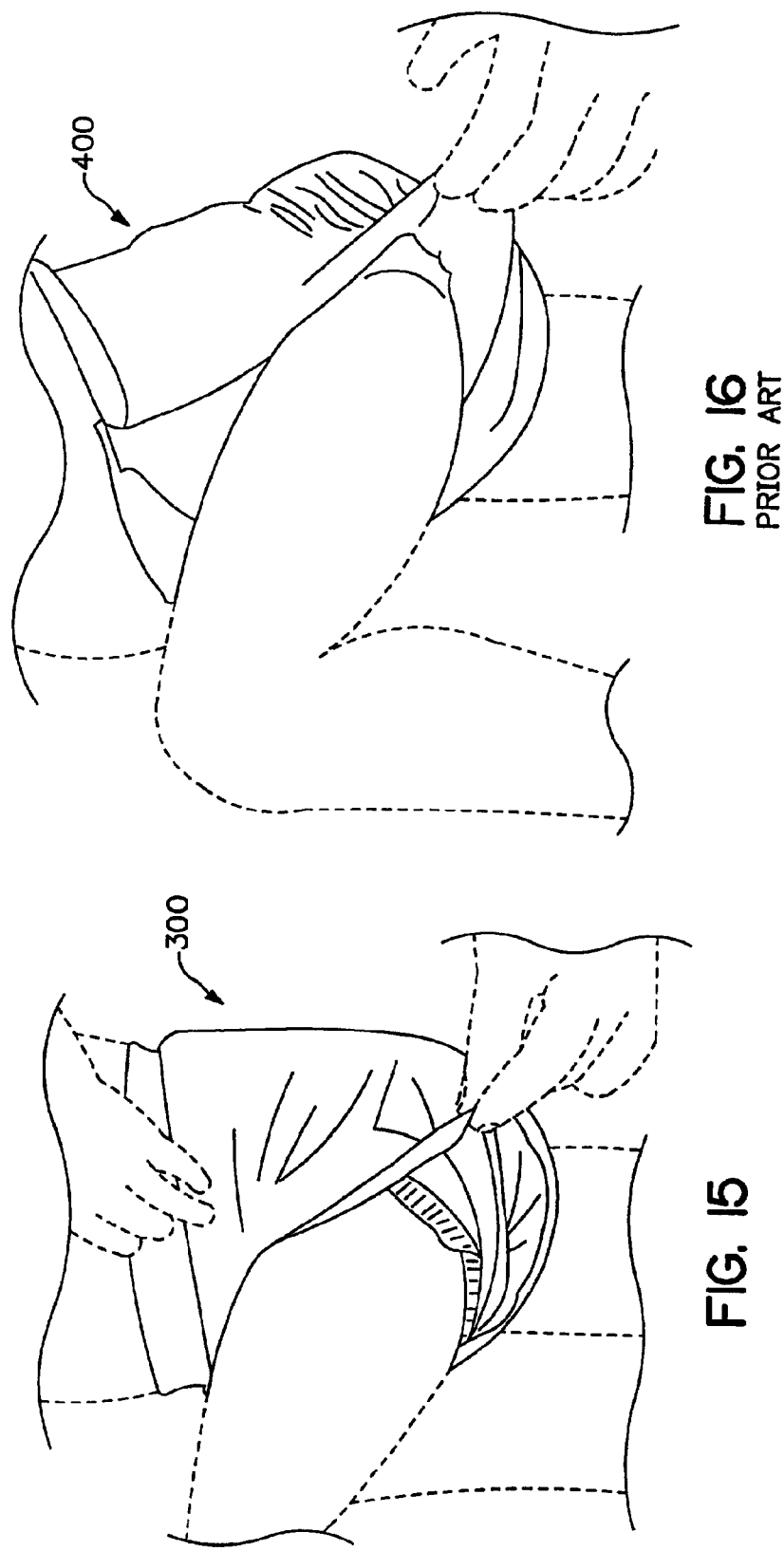

INDEPENDENCE OF COMPONENTS IN ABSORBENT ARTICLES

CROSS REFERENCE TO RELATED APPLICATION

This application is a continuation-in-part application of application Ser. No. 09/698,517, filed on 27 Oct. 2000. The co-pending parent application is hereby incorporated by reference herein and is made a part hereof, including but not limited to those portions which specifically appear hereinafter.

FIELD OF THE INVENTION

This invention relates generally to absorbent articles for absorbing body fluids and exudates.

One aspect of the present invention more particularly relates to such absorbent articles which desirably self-form seals at natural body hinge points of a wearer.

Another aspect of the present invention more particularly relates to such absorbent articles which generally desirably provide improved or increased independence of the components thereof.

Still another aspect of the present invention more particularly relates to such absorbent articles which include in-captured leg elastics such as may desirably simplify manufacture and production and the costs associated therewith.

BACKGROUND OF THE INVENTION

A wide variety of types of structures are known in the art for use in or as absorbent articles, particularly disposable absorbent articles, such as used to collect various body fluids and exudates. In particular, various commercial absorbent articles having a pant-like form are known and/or available. For example, typical such commercial absorbent articles include: adult incontinence garments, diapers for infant and children, training pants and swim wear garments.

Disposable articles of these types generally comprise components for receiving, absorbing and retaining fluids. Typically, the components of such articles include a liquid permeable topsheet, an absorbent core and a liquid impermeable backsheet.

The human body is generally composed of a plurality of compound, as opposed to unidirectional, curves. The curves of the human body are particularly complicated at locations where limbs, such as arms and legs, join the torso. The curves can also be associated with hinge points of the body. For example, the curves associated with where the legs join the torso define hinge areas that are capable of moving in relationship to each other. When an absorbent article is donned by a wearer, the hinge areas (such as the leg and waist openings) are defined by compound curves—not straight lines. Hinge areas tend to be the areas of absorbent articles that are most susceptible to leakage. Conventional absorbent articles, however, are primarily rectangular in shape and thus provide limited curvature in their components. Consequently, conventional absorbent articles are generally not optimal for providing close-fitting seals between the edges of the absorbent article and the skin of the wearer. As a result, undesirable leakages may occur or be experienced with the use of such absorbent articles. In an effort to compensate for the lack of a close, custom fit and to provide desired or required skin coverage, conventional absorbent articles commonly incorporate certain oversized components or elements, such as rectangular absorbent pads in the crotch region or area of the article.

Present day diapers commonly include stretchable side panels such that the garment is better able to conform to the contours of the body of the wearer. Other components of such present day articles, such as outer covers, bodyside liners and absorbent assemblies, for example, however, typically remain totally or at least primarily non-extensible or unstretchable. As a result, when such a garment is worn, only the side panels can stretch.

In addition, such absorbent article garments and/or specific portions thereof are typically subjected to a wide range of stresses such as may vary dependent on the size and movements of the wearer. Unfortunately, however, various conventional diapers do not allow or permit these stresses to be relieved except by degradation of fit. Further, where the stresses are not appropriately relieved, the wearer may experience discomfort as well as red-marking of or on the skin of the wearer. As will be appreciated, fit degradation commonly results or produces a concomitant degradation in the protection against leakage provided by the diaper article. Further, when such conventional diapers degrade with extended wear time, the side panels typically narrow such as to concentrate forces along the sides at the fastening region of the diaper. The resulting high force loads on the fastening region of the diaper often leads to fastener failure, further or increased wearer discomfort, and/or further or increased red-marking of the skin of the wearer.

Also, as a result of a general inability for many diaper designs to adapt to differences in infant shapes, some conventional diapers are difficult to apply onto an intended wearer. Further difficulty may be encountered by the tendency of a conventional diaper to fold back on itself or otherwise curl-up prior to application to an infant. Also, many conventional diapers do not hold the target area portions of the liner and absorbent desirably sufficiently close to the body, thus resulting in increased opportunity for bodily wastes to spread along the skin before such bodily wastes have been appropriately absorbed by or in the diaper.

Further, it is common for diaper articles to include waist elastic members and leg elastic members, respectively, in an effort to enhance containment and/or absorption of body exudates. The outer cover and bodyside liner components of present day absorbent articles, such as diapers, are generally not made of elastic or stretchable materials. In most commercial products, such leg elastics are captured between the outer cover and the liner which results in the outer cover and the liner necessarily being wider and longer than the torso measurements in order to be capable of appropriately accommodating the stresses applied on the chassis when the product has been positioned in the crotch region of a wearer. In addition, in such designs the leg elastics are well beyond (outboard) of the natural bodylines in the crotch region. Also, the leg elastic can be placed in a curved orientation so as to conform to the curved contour typically created by the absorbent article chassis to provide a respective opening wherethrough a leg of the wearer may pass.

In view of the above, there is a need and a demand for improved absorbent articles.

In particular, there is a need and a demand for absorbent articles, such as form-fitting, pant-like, personal care absorbent garments, which desirably self-form seals at natural body hinge points of a wearer.

There is a further need and desire for such absorbent articles which generally desirably provide improved or increased independence of the components thereof.

There is a still further need and demand for such absorbent articles which include in-captured leg elastics such as may desirably simplify either or both manufacture and production and the costs associated therewith.

SUMMARY OF THE INVENTION

A general object of the invention is to provide an improved absorbent article for absorbing body fluids and exudates.

A more specific objective of the invention is to overcome one or more of the problems described above.

As detailed below, the general object of the invention can generally be attained through various specifically constructed absorbent articles. Absorbent articles, in accordance with various embodiments of the invention, generally have or include a front waist area forming a front edge, a back waist area forming a back edge, and a crotch area disposed between the front and back waist areas.

In accordance with one embodiment of the invention, the general object of the invention can be attained, at least in part, through a self-forming seal absorbent article adapted to be worn by a wearer having a body contour. Such an absorbent article includes a chassis having opposed first and second longitudinal sides and opposed first and second lateral sides. The chassis also provides a footprint contour adapted to match the body contour of a wearer of the absorbent article. In accordance with one preferred embodiment, the chassis includes a biaxially extensible outer cover, a biaxially extensible bodyside liner forming a wearer adjacent surface, a biaxially extensible absorbent core assembly interposed between the outer cover and the bodyside liner, and a pair of laterally-spaced apart and longitudinally-extending containment flap members disposed along the wearer adjacent surface of the bodyside liner, each of the containment flap members comprises a material extensible in at least one of the longitudinal and lateral directions.

In accordance with another embodiment of the invention, the general object of the invention can be attained, at least in part, through an absorbent article which includes a chassis having opposed first and second longitudinal sides, opposed first and second lateral sides, an original longitudinal length, an original lateral length and which chassis has components including: an outer cover, a bodyside liner and an absorbent core assembly interposed between the outer cover and the bodyside liner. In such an article of construction, the outer cover forms a cover perimeter and the bodyside liner forms a wearer adjacent surface and a liner perimeter. Further, the chassis includes a perimeter area and an interior area, wherein the perimeter area is defined at least in part by the cover perimeter and the liner perimeter and wherein the interior area is free of bonding.

In accordance with yet another embodiment of the invention, the general object of the invention can be attained, at least in part, through an absorbent article which includes a chassis having opposed first and second longitudinal sides, opposed first and second lateral sides, an original longitudinal length, an original lateral length and which chassis defines first and second leg openings and includes: a biaxially extensible outer cover, a biaxially extensible bodyside liner forming a wearer adjacent surface, an absorbent core assembly interposed between the biaxially extensible outer cover and the biaxially extensible bodyside liner, a first leg elastic member captured between the biaxially extensible outer cover and the biaxially extensible bodyside liner along the first lateral side of the chassis and a second leg elastic member captured between the biaxially extensible outer cover and the biaxially extensible bodyside liner along the second lateral side of the chassis.

The prior art generally fails to provide a design or construction for absorbent articles that desirably provides or results in form-fitting, pant-like, personal care absorbent garments, which desirably self-form seals at natural body hinge points of a wearer. Further, the prior art generally fails to provide a design or construction for absorbent articles that provide improved or increased independence of the components thereof to the extent desired in various applications. Still further, the prior art generally fails to provide a design or construction for absorbent articles that desirably include in-captured leg elastics such as may desirably simplify either or both manufacture and production of the absorbent article and reduce the costs associated therewith.

With the absorbent articles of the invention, the area of the article including all of the chassis components (e.g., outer cover, absorbent core and liner) is generally reduced. It is particularly desirable to reduce the number of materials present in the areas of the leg and waist openings. The assembly of complete chassis materials can be replaced with thinner and more pliable materials capable of curving and conforming with the hinge areas. The seals formed by such materials tend not to form rugosities, bunching, folding, curling or other deformation of the material that can interfere with the article's performance. Self-forming seals can adjust to the shape of individual wearers.

The invention further comprehends a self-forming seal absorbent article such that includes a chassis having opposed first and second longitudinal sides and opposed first and second lateral sides. The chassis also has an original longitudinal length and an original lateral length. The chassis further also provides a footprint contour adapted to match the body contour of a wearer of the absorbent article.

More particularly, such a chassis may desirably include: a biaxially stretchable outer cover, a biaxially stretchable bodyside liner forming a wearer adjacent surface, a biaxially stretchable absorbent core assembly interposed between the outer cover and the bodyside liner, and a pair of laterally-spaced apart and longitudinally-extending containment flap members disposed along the wearer adjacent surface of the bodyside liner, each of the containment flap members being extensible in at least one of the longitudinal and lateral directions. In accordance with a particularly preferred embodiment of the invention, such a chassis can be longitudinally stretched at least 5 percent and up to 150 percent of its original longitudinal length and laterally stretched at least 10 percent and up to 200 percent of its original lateral length.

The invention also comprehends an absorbent article such as adapted to be worn by a wearer and which absorbent article includes a front waist area forming a front edge, a back waist area forming a back edge, and a crotch area disposed between the front and back waist areas. The absorbent article also includes a chassis. The chassis has opposed first and second longitudinal sides and opposed first and second lateral sides. The chassis also has an original longitudinal length and an original lateral length. The chassis further comprises components including; an outer cover forming a cover perimeter, a bodyside liner forming a wearer adjacent surface and a liner perimeter, and an absorbent core assembly interposed between the outer cover and the bodyside liner. The chassis includes a perimeter area and an interior area, wherein the perimeter area is defined at least in part by the cover perimeter and the liner perimeter and wherein the interior area is free of bonding.

The invention further comprehends a self-forming seal absorbent article adapted to be worn by a wearer having a body contour and which absorbent article including a front waist area forming a front edge, a back waist area forming a back edge, and a crotch area disposed between the front and back waist areas. The absorbent article includes a chassis having opposed first and second longitudinal sides and opposed first and second lateral sides. The chassis also provides a footprint contour adapted to match the body contour of a wearer of the absorbent article. The chassis includes a biaxially extensible outer cover, a biaxially extensible bodyside liner forming a wearer adjacent surface, a biaxially extensible absorbent core assembly interposed between the outer cover and the bodyside liner, and a pair of laterally-spaced apart and longitudinally-extending containment flap members disposed along the wearer adjacent surface of the bodyside liner, each of the containment flap members comprises a material extensible in at least one of the longitudinal and lateral directions. The chassis includes a perimeter area and an interior area, wherein the perimeter area is defined at least in part by the cover perimeter and the liner perimeter and wherein the interior area is free of bonding.

The invention still further comprehends a self-forming seal absorbent article adapted to be worn by a wearer having a body contour. The absorbent article includes a front waist area forming a front edge, a back waist area forming a back edge, and a crotch area disposed between the front and back waist areas. The absorbent article further includes a biaxially stretchable chassis having opposed first and second longitudinal sides and opposed first and second lateral sides. The chassis has an original longitudinal length and an original lateral length. The chassis also provides a footprint contour adapted to match the body contour of a wearer of the absorbent article. The chassis includes: a biaxially stretchable outer cover, a biaxially stretchable bodyside liner forming a wearer adjacent surface, a biaxially stretchable absorbent core assembly interposed between the outer cover and the bodyside liner, and a pair of laterally-spaced apart and longitudinally-extending containment flap members disposed along the wearer adjacent surface of the bodyside liner, each of the containment flap members being extensible in at least one of the longitudinal and lateral directions. The further includes a perimeter area and an interior area, wherein the perimeter area is defined at least in part by the cover perimeter and the liner perimeter and wherein the interior area is free of bonding. Further, the chassis can be longitudinally stretched at least 5 percent and up to 150 percent of its original longitudinal length and laterally stretched at least 10 percent and up to 200 percent of its original lateral length.

The invention additionally comprehends an absorbent article adapted to be worn by a wearer and which absorbent article has a front waist area forming a front edge, a back waist area forming a back edge, and a crotch area disposed between the front and back waist areas. The absorbent article also includes a chassis having opposed first and second longitudinal sides and opposed first and second lateral sides. The chassis has an original longitudinal length and an original lateral length. The chassis defines first and second leg openings. The chassis includes: a biaxially extensible outer cover, a biaxially extensible bodyside liner forming a wearer adjacent surface, an absorbent core assembly interposed between the biaxially extensible outer cover and the biaxially extensible bodyside liner, a first leg elastic member captured between the biaxially extensible outer cover and the biaxially extensible bodyside liner along the first longitudinal side of the chassis and a second leg elastic member captured between the biaxially extensible outer cover and the biaxially extensible bodyside liner along the second longitudinal side of the chassis.

The invention additionally further comprehends such an absorbent article wherein each of the first and second longitudinal sides forms a straight edge and wherein at least one of the first and second leg elastic members comprises an elastic film material.

As used herein, "extensible" and the like refer to that property of a material, member, element or composite by virtue of which it tends to be extended beyond its original size and shape upon application of a force causing a deformation.

Further, "stretchable" and the like refer to that property of a material, member, element or composite by virtue of which it tends to recover its original size and shape after removal of a force causing a deformation. In connection therewith, "elastic," "elasticized," "elasticity" and the like also generally refer to that property of a material, member, element or composite by virtue of which it tends to recover its original size and shape after removal of a force causing a deformation.

"Biaxial extensibility" refers to a material having extensibility in two directions perpendicular to one another, e.g., extensibility in a machine direction and in a cross direction, or in a longitudinal direction (front to back) and a lateral direction (side to side).

"Biaxial stretch" refers to a material having stretchability in two directions perpendicular to one another, e.g., stretchability in a machine direction and in a cross direction, or in a longitudinal direction (front to back) and a lateral direction (side to side).

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Layer," when used herein in the singular, can have the dual meaning of a single element or a plurality of elements.

"Longitudinal" and "lateral" have their customary meaning, as indicated by the longitudinal and lateral axes depicted in FIG. 2. The longitudinal axis lies in the plane of the article and is generally parallel to a vertical plane that bisects a standing wearer into left and right body halves when the article is worn. The lateral axis lies in the plane of the article generally perpendicular to the longitudinal axis. The article as illustrated is longer in the longitudinal direction than in the lateral direction.

"Longitudinal extensibility" refers to extensibility in the longitudinal direction along the longitudinal axis.

"Longitudinal stretch" refers to stretchability in the longitudinal direction along the longitudinal axis.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 decitex, and are generally self-bonding when deposited onto a collecting surface. Meltblown fibers used in the present invention are preferably substantially continuous in length.

"Microfibers" are small diameter fibers typically having an average fiber denier of about 0.005–10. Fiber denier is defined as grams per 9000 meters of a fiber. For a fiber having circular cross-section, denier may be calculated as fiber diameter in microns squared, multiplied by the density in grams/cc, multiplied by 0.00707. For fibers made of the same polymer, a lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 calculated as ($15^2 \times 0.89 \times 0.00707 = 1.415$). Outside the United States the unit of measurement is more commonly the "tex," which is defined as the grams per kilometer of fiber. Tex may be calculated as denier/9. A decitex is 0.1 of a tex.

"Necked" or "neck-stretched" interchangeably refer to a method of elongating a nonwoven fabric, generally in the longitudinal, or machine direction, to reduce its width in a controlled manner to a desired amount. The controlled stretching may take place under cool, room temperature or greater temperatures and is limited to an increase in overall dimension in the direction being stretched up to the elongation required to break the fabric, which in most cases is about 1.2 to 1.4 times. When relaxed, the web retracts toward its original dimensions. Such a process is disclosed, for example, in U.S. Pat. No. 4,443,513 to Meitner and Notheis, U.S. Pat. Nos. 4,965,122, 4,981,747 and 5,114,781 to Morman and U.S. Pat. No. 5,244,482 to Hassenboehler Jr. et al.

"Nonwoven" and "nonwoven web" refer to fibrous materials and webs of fibrous material which are formed without the aid of a textile weaving or knitting process.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a polymer material that softens and flows when exposed to sufficient heat and which substantially returns to a nonsoftened condition when cooled to room temperature.

Other objects and advantages will be apparent to those skilled in the art from the following detailed description taken in conjunction with the appended claims and drawings.

BRIEF DESCRIPTION OF THE DRAWINGS

FIG. 15 is a simplified side perspective view of the absorbent garment article shown in FIG. 11 as it is applied to the torso of a wearer and showing the inner containment flap.

FIG. 16 is a corresponding simplified side perspective view of the prior art absorbent garment article shown in FIG. 12 as applied to the torso of a wearer and showing the inner containment flap thereof.

DETAILED DESCRIPTION OF THE INVENTION

The present invention, as is described in more detail below, provides an improved absorbent article for absorbing body fluids and exudates. In particular, absorbent article configurations and constructions in accordance with the invention desirably provide improvements with respect to at least one, preferably at least two and, more preferably all three of the absorbent article qualities or properties of fit, comfort and containment capability for body fluids and exudates. As detailed below, absorbent articles, in accordance with at least certain preferred embodiments of the invention, involve the selection and use of certain specified materials in certain specific absorbent article constructions.

In accordance with one aspect of the invention, absorbent articles, such as form-fitting, pant-like, personal care absorbent garments, which desirably self-form seals between the absorbent article, e.g., the edges thereof, and the skin of the wearer, at natural body hinge points of a wearer are provided. In accordance with another aspect of the invention, there are provided absorbent articles which generally desirably provide or result in improved or increased independence of the components in order to improve the fit of the articles. In accordance with another aspect of the invention there are provided absorbent articles of specific construction and which include captured leg elastics that improve the garment-like fit at the leg and provide targeted stretch and recovery in multiple directions without a high degree of pre-tension and recovery. Captured leg elastics may also desirably simplify either or both manufacture and production and the costs associated therewith.

Figure 1:
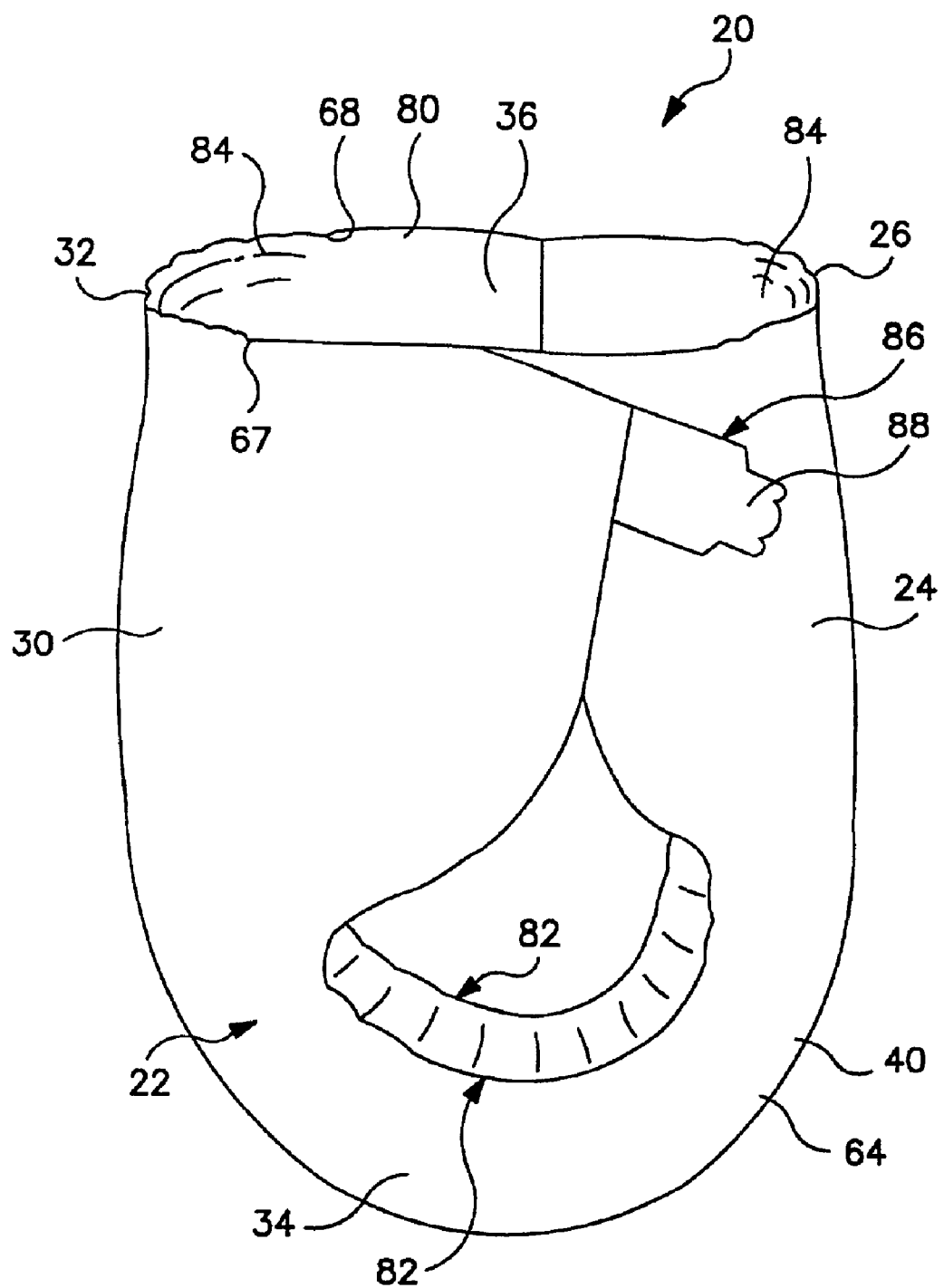
FIG. 1 is a side perspective view of an absorbent garment article, in accordance with one preferred embodiment of the invention, in a fastened position.
Figure 2:
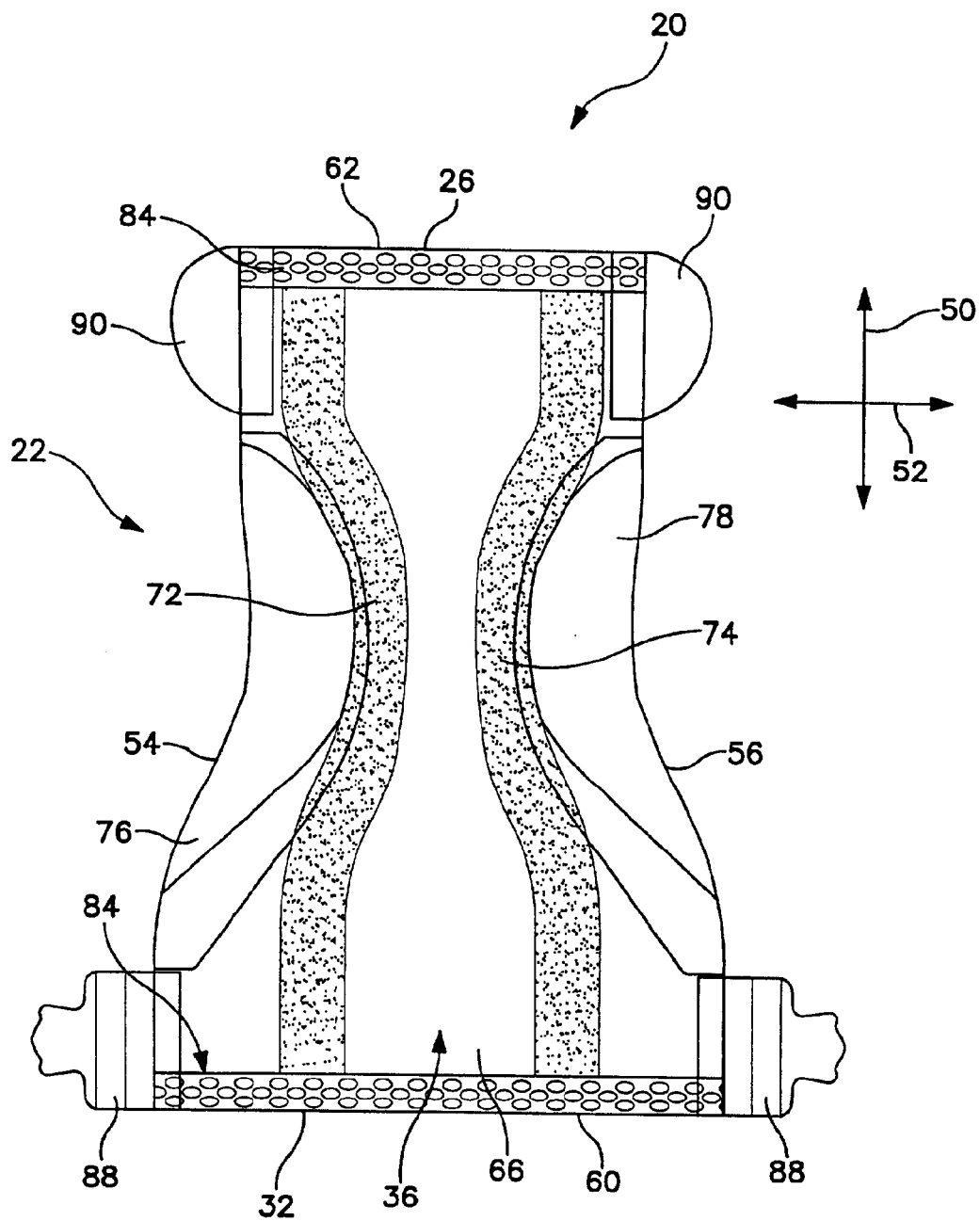
FIG. 2 is a simplified plan schematic view of the absorbent garment article shown in FIG. 1 and showing the surface of the article that faces the wearer when the article is worn.

Referring initially to FIGS. 1 and 2, there is illustrated a disposable absorbent article, in accordance with one preferred embodiment of the invention and generally designated by the reference numeral 20. FIG. 1 illustrates the absorbent garment article 20 in a fastened position. FIG. 2 illustrates the absorbent garment article 20 in a simplified plan schematic view, showing the surface of the article that faces the wearer when the article is worn. As will be appreciated, the absorbent article 20 has the general form of a disposable diaper such as adapted to be worn about the lower torso by an infant. It is to be understood, however, that while the invention is described below with particular reference to disposable diapers such as for an infant or a child, the broader practice of the invention is not necessarily so limited. For example, the invention can, if desired, be applied to other forms or types of absorbent articles including various disposable absorbent articles such as are generally configured to collect and contain human discharges or exudates such as, including, urine and fecal material and which articles also desirably avoid leakage of such discharge materials. Other examples of such suitable articles include adult incontinence garments, training pants and swim wear garments as well as other personal care or health care garments, or the like.

The diaper absorbent article 20 generally includes a chassis 22 and further includes or defines a front waist area or region 24 forming a front edge 26, a back waist area or region 30 forming a back edge 32, and a crotch area or region 34 disposed between the front and back waist areas, 24 and 30, respectively. The waist area 24 includes the portion of the diaper 20 which, when worn, is positioned on the front of the wearer while the back waist area 30 includes the portion of the diaper which, when worn, is positioned on the back of the wearer. The crotch region 34 includes that portion of the diaper 20 which, when worn, is positioned between the legs of the wearer and covers the lower torso of the wearer. The diaper absorbent article 20 forms or includes an inner surface 36 which is configured to contact the wearer, and an outer surface 40 opposite the inner surface 36 and such as configured to contact the wearer's clothing.

Figure 3:
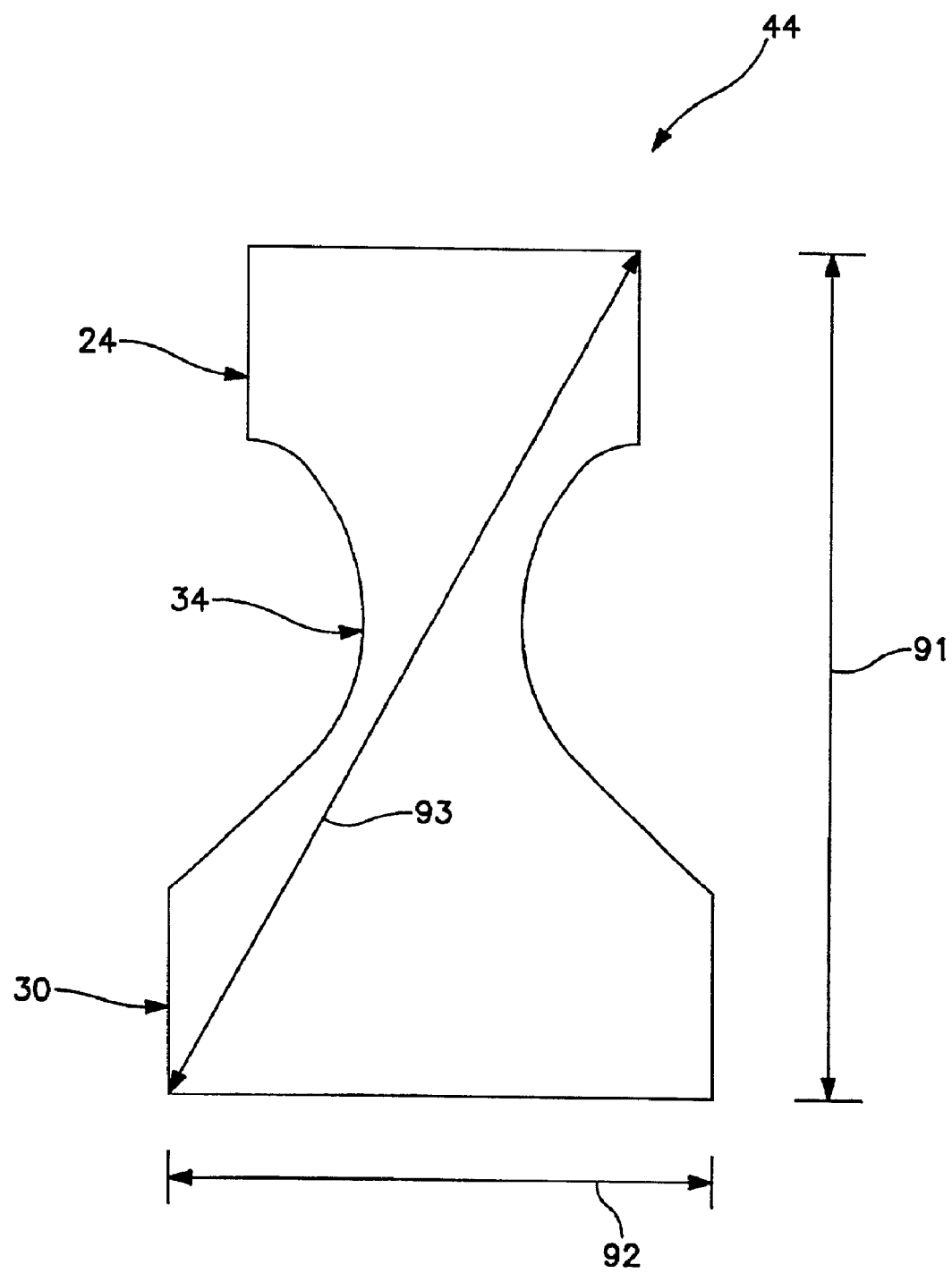
FIG. 3 is a simplified plan view of the footprint contour of the chassis of the absorbent garment article, shown in FIGS. 1 and 2, shown in isolation.

FIG. 3 illustrates the general footprint contour 44 of the absorbent chassis 22, shown in isolation with the front waist area 24, back waist area 30 and crotch area 34 accordingly designated. As shown, such footprint contour generally corresponds to the outline formed by the chassis without the inclusion of fastener flaps and the like. The absorbent chassis 22 is generally conformable and capable of absorbing or otherwise appropriately retaining body exudates. In general, the size and absorbent capacity of the absorbent chassis 22 are selected for compatibility with the size of the intended wearer and the fluid loading imparted by the intended use of the absorbent article 20. In accordance with the one preferred embodiment of the invention, the footprint contour 44 is, as shown, adapted to match the body contour of the projected or anticipated wearer of the absorbent article. To that end, it is generally preferred that absorbent chassis used in the practice of the invention be narrower in the crotch area 34 as compared to the front waist and back waist areas, 34 and 30, respectively. It has been found that absorbent chassis for use in the practice of the invention are particularly useful when the width dimension in the crotch area 34 is from about 2.5 to about 10.2 centimeters (from about 1 to about 4 inches), preferably having a crotch area width of no more than about 7.6 centimeters (3 inches) and, more preferably, having a crotch area width of no more than about 5.1 centimeters (2 inches). Such crotch width dimensions for absorbent articles and chassis in accordance with the invention have been found to generally result in a better fit of the absorbent article on a wearer, particularly between the legs of the wearer.

Figure 26A:
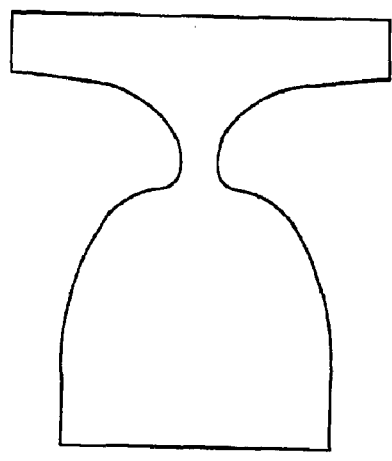
FIG. 26A is a line drawing showing the body profile of the diapering area for an average infant weighing 16–28 pounds (7–13 kg) in a sitting position.
Figure 26B:
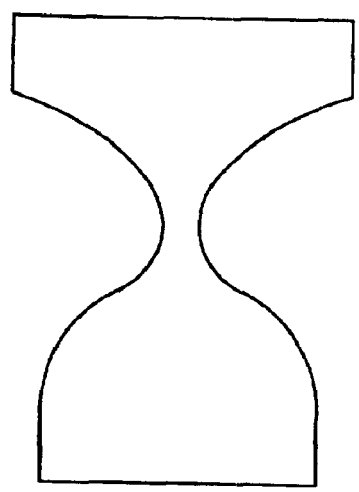
FIG. 26B is a line drawing showing the body profile of the diapering area for an average infant weighing 16–28 pounds (7–13 kg) in a standing position.
Figure 27:
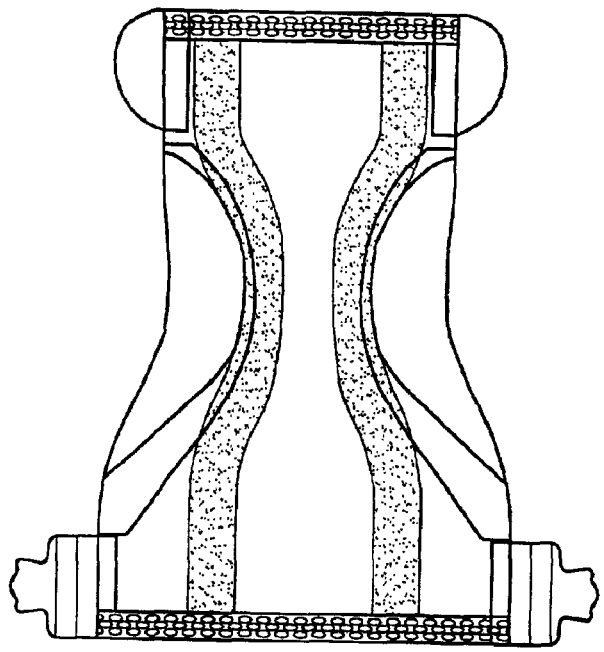
FIG. 27 is a simplified plan schematic view of the absorbent garment article shown in FIG. 1 and generally similar to FIG. 2 and here included to facilitate comparison relative to FIGS. 26A and 26B.

To more fully appreciate the invention, reference is now made to FIG. 26A and FIG. 26B which are line drawings showing the body profile of the diapering area for an average infant weighing 16–28 pounds (7–13 kg) in a sitting position and in a standing position, respectively, and FIG. 27 which is a simplified plan schematic view of the absorbent garment article shown in FIG. 1 and generally similar to FIG. 2. As shown, absorbent garment articles in accordance with the invention desirably have or provide a contour which closely matches that of the body of a wearer. Various of the advantages resulting or relating thereto are more fully described and detailed elsewhere herein.

Returning to FIG. 2, for ease of reference there are included arrows 50 and 52 depicting the orientation of the longitudinal and the lateral or transverse axis, respectively, for the diaper absorbent article 20. Thus, as shown in FIG.

2, the chassis 22 has opposed longitudinal sides 54 and 56, respectively, and opposed lateral sides 60 and 62, respectively.

Figure 4:
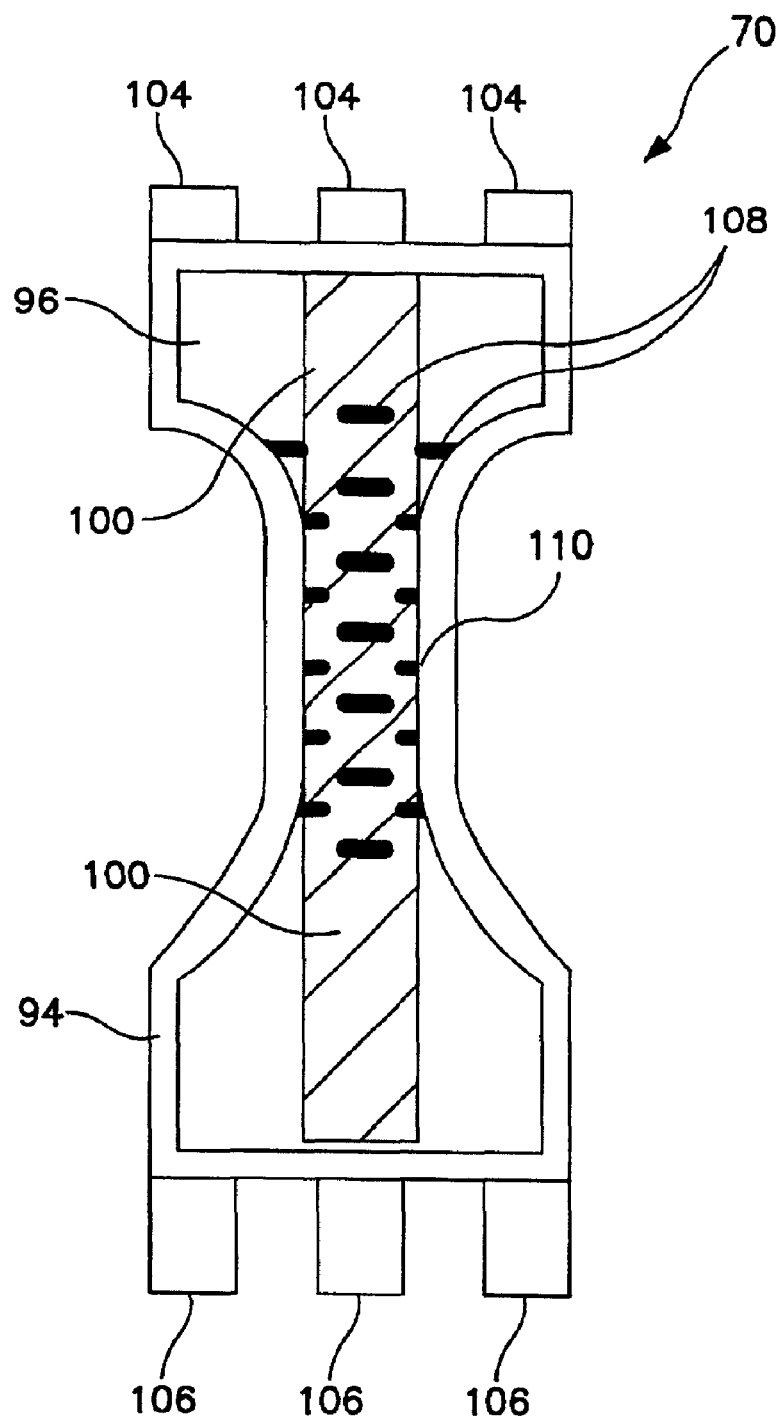
FIG. 4 is a schematic plan view of an absorbent assembly suitable for use in the absorbent garment article shown in FIGS. 1 and 2.

As will be appreciated, the absorbent chassis 22 is desirably generally configured to contain and/or absorb body exudates discharged from the wearer. To that end and as shown in FIGS. 1 and 2, the diaper 20 and, specifically, the chassis 22 includes an outer cover 64 such as serves, at least in part, to form the outer surface 40, and a bodyside liner 66 such as serves, at least in part, to form the inner or wearer adjacent surface 36. The outer cover 64 forms or includes a cover perimeter 67. The bodyside liner 66 similarly forms or includes a liner perimeter 68. The outer cover 64 and the bodyside liner 66 are joined or connected, such as described in greater detail below, in a superposed relation. An absorbent core assembly 70, such as shown in FIG. 4 and as described in greater detail below, is interposed or otherwise located between the outer cover 64 and the bodyside liner 66.

Further, in accordance with a preferred embodiment of the invention, the diaper 20 and, specifically, the chassis 22 includes a pair of laterally-spaced apart and longitudinally-extending containment flap or gasket members, 72 and 74, respectively, such as disposed along the wearer adjacent surface 36 of the bodyside liner 66 and which are configured to provide a barrier to the transverse or lateral flow of body exudates. The containment flap members 72 and 74 each generally define an unattached edge which assumes an upright, generally perpendicular configuration in at least the crotch area 34 of the diaper 20 to form a seal against the wearer's body. Containment flap member constructions and arrangements are generally well known to those skilled in the art and are described in U.S. Pat. No. 4,704,116 issued Nov. 3, 1987 to Enloe, which is incorporated herein by reference.

The diaper absorbent article 20 further includes a pair of oppositely disposed leg extended elements 76 and 78, respectively, continuous with or otherwise generally laterally extending from either or both the outer cover 64 and the bodyside liner 66 of the chassis 22 at the longitudinal sides 54 and 56, respectively, thereof. In such a diaper absorbent element configuration, the leg cuff elements 76 and 78 desirably serve as leg elastic elements which outwardly extend from the absorbent core of the diaper article 20. While the invention can be practiced with absorbent articles which include such leg cuff elements, the invention can, if desired, alternatively incorporate and employ an encased or captured leg elastic such as described in greater detail below.

As shown in the diaper 20 in FIG. 1, the crotch area 34 and front and back waist areas 24 and 30 together define a three-dimensional pant configuration having a waist opening 80 and a pair of leg openings 82. The waist edges 26 and 32 are configured to encircle the waist of a wearer when worn and provide the waist opening 80 which defines a waist perimeter dimension.

To further enhance containment and/or absorption of body exudates, the diaper 20 can include waist elastic members 84, as are known to those skilled in the art. The waist elastic members 84 can be operatively joined to the outer cover 64 and/or the bodyside liner 66, and can extend over part or all of the waist edges 26 and 32.

The diaper 20 also includes a fastening system 86, such as known in the art and such as operatively attached to the outer cover 64 along the longitudinally extending sides 54 and 56, just below the waist edges 32 and 26. As shown, the fastening system 86 can include a pair of laterally-opposed back fastener tabs 88 that can be fastened directly to the front waist area or region 24 of the absorbent article 20, as shown in FIG. 1, by suitable means, such as mechanical fasteners, for example. As will be appreciated, other fastener systems or means can, if desired, be used in the practice of the invention and thus the broader practice of the invention is to be understood as not limited by or to the incorporation or use of specific fastening systems or techniques. The diaper 20 also includes front flaps or ears 90 such as known in the art and such as may be desired for various reasons such as to better provide or ensure a snug fit of the diaper article onto the torso of a wearer, for example.

In accordance with one aspect of the invention, a chassis which provides a footprint contour adapted to match the body contour of a wearer of the absorbent article (as shown in FIGS. 26A and 26B) is desirably combined with specifically selected materials of construction and article configuration to provide or result in an article that self-forms seals at natural body hinge points of a wearer. In one preferred embodiment of the invention, the outer cover 64, the bodyside liner 66 and the absorbent core assembly 70 are each formed of materials or constructed to be biaxially extensible and each of the containment flap members 72 and 74 comprises a material extensible in at least one of the longitudinal and lateral directions.

Returning to FIG. 3, the general footprint contour 44 is shown with longitudinal, lateral and diagonal directions designated by the reference numerals 91, 92 and 93, respectively. While the invention can desirably be practiced to produce absorbent articles which self-form seals wherein the chassis provides various selected degrees of extensibility and, in at least certain preferred embodiments stretchability, absorbent articles wherein the chassis can be extended in the longitudinal direction 91 at least 5 percent and up to 150 percent of its original longitudinal length are generally preferred; with absorbent articles wherein the chassis can be extended in the longitudinal direction 91 at least 15 percent and up to 125 percent of its original longitudinal length generally being more preferred; and with absorbent articles wherein the chassis can be extended in the longitudinal direction 91 at least 30 percent and up to 100 percent of its original longitudinal length generally being most preferred. Correspondingly, absorbent articles wherein the chassis can be extended in the lateral direction 92 at least 10 percent and up to 200 percent of its original lateral length are generally preferred, with absorbent articles wherein the chassis can be extended in the lateral direction 92 at least 25 percent and up to 150 percent of its original lateral length generally being more preferred, and with absorbent articles wherein the chassis can be extended in the lateral direction 92 at least 50 percent and up to 125 percent of its original lateral length generally being most preferred. Further, absorbent articles wherein the chassis can be extended in the diagonal direction 93 at least 10 percent and up to 200 percent of its original diagonal length are generally preferred; with absorbent articles wherein the chassis can be extended in the diagonal direction 93 at least 25 percent and up to 150 percent of its original diagonal length generally being more preferred; and with absorbent articles wherein the chassis can be extended in the diagonal direction 93 at least 50 percent and up to 125 percent of its original diagonal length being most preferred. Absorbent articles with such extensibility are in sharp contrast to current absorbent articles which have a non-extensible chassis, e.g., have a chassis which can be extended a) in the longitudinal direction only about 5 percent of its original longitudinal length, b) in the lateral direction only about 5 percent of its original lateral length, and c) in the diagonal direction only about 1 percent of its original diagonal length.

Further, in accordance with certain preferred embodiments, one or more and, in certain cases, each of the outer cover 64, the bodyside liner 66 and the absorbent core assembly 70 can be formed of materials or constructed to be biaxially stretchable. For example, in certain preferred embodiments absorbent articles in accordance with the invention desirably have longitudinal, lateral and diagonal stretchabilities that generally correspond to the extendibilities set forth above.

Still further, in accordance with certain preferred embodiments, each of the pair of containment flap members 72 and 74 desirably comprises a material extensible in both the longitudinal and lateral directions.

Yet still further, in accordance with certain preferred embodiments, each of the pair of containment flap members 72 and 74 desirably comprises a biaxially stretchable material.

Suitable materials for the biaxially extensible outer cover 64 include biaxially extensible materials and biaxially elastic stretchable materials. One example of a suitable outer cover material for use in the practice of the invention is composed of 0.3 ounces per square yard (osy) polypropylene spunbond, necked and creped at about 50% and that is laminated with 3 grams per square meter (gsm) Findley 2525A styrene-isoprene-styrene-based adhesive to 10 gsm PEBAX® 2533 film and such as provides a longitudinal and lateral elongation optimum of between 100%–200% and a tension at 50% extension preferably between 50–600 g, with an optimum of between 100–400 g, as measured on 3-inch wide material.

Suitable materials for the biaxially extensible bodyside liner 66 include biaxially extensible materials and biaxially elastic stretchable materials. One example of a suitable bodyside liner material for use in the practice of the invention is composed of 0.3 osy polypropylene spunbond, necked and creped at about 50% and treated with about 0.7 weight percent of a surfactant such as AHCOVEL® from Hodgson Textile Chemicals of Mount Holly, N.C., U.S.A.

Suitable materials for the containment flap members 72 and 74 include materials extensible in at least one of the longitudinal and lateral directions, materials stretchable in at least one of the longitudinal and lateral directions, materials which are biaxially extensible and materials which are biaxially elastic stretchable. An example of a suitable containment flap material is polypropylene spunbond necked and creped at about 50% with Findley HX 2695 Elastic Barrier Adhesive strands or slot coated.

For those embodiments which incorporate a leg cuff, a suitable material of construction for the leg cuffs 76 and 78 which, as described above, generally refers to such wearer leg adjacent portion which extends beyond the cover outer edge, is an Elastic Barrier Adhesive such as constituting 110 gsm Findley HX 2695 adhesive at 750% elongation with 0.6 osy prism facings on both sides. Suitable encased leg elastic materials for use in alternative embodiments of the invention can desirably constitute such an Elastic Barrier Adhesive without the facings. Waist elastics used in the absorbent articles of the invention may also be formed of such materials. In addition, low tension spandex fibers sold under the trade name LYCRA® available from E.I. du Pont de Nemours and Company, Wilmington, Del., U.S.A., may be used as a suitable leg and/or waist elastic.

The waist elastic members 84 used in the practice of the invention can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the waist elastic members 84 include a plurality of dry-spun coalesced multifilament spandex elastomeric threads sold under the trade name LYCRA®. In another particular embodiment, for example, the waist elastic members 84 include Findley HX 2695-01 adhesive laminated to two facings of 0.6 osy bicomponent polypropylene/polyethylene spunbond. Alternatively, up to about six strands of 310 decitex LYCRA® may be also laminated at 250% elongation between the spunbond facings in addition to the Findley adhesive.

FIG. 4 is a schematic plan view of the absorbent core assembly 70, in accordance with one embodiment of the invention and suitable for use in the absorbent garment article shown in FIGS. 1 and 2. As identified above, the absorbent core assembly 70 is desirably formed of materials or otherwise constructed to be biaxially extensible. Further, in accordance with certain preferred embodiments of the invention, the absorbent core assembly is desirably formed of materials or otherwise constructed to be biaxially and diagonally stretchable. Those skilled in the art and guided by the teachings herein provided will appreciate that absorbents or absorbent core assemblies used in the practice of the invention need not necessarily be stretchable. For example, in accordance with certain embodiments, the absorbent or absorbent core assembly can be: (1) non-extensible; (2) machine direction (MD) extensible; (3) cross direction (CD) extensible; or (4) biaxially extensible.

The absorbent core assembly 70 includes a carrier layer 94, a full pad continuous layer 96, and a notched absorbent core 100. In the illustrated embodiment, the carrier layer 94 extends beyond the absorbent region of the assembly 70 to form either or both front and back tails 104 and 106, respectively. The tails 104 and 106 are joined or attached to the respective front and back waist edges 26 and 32, of the bodyside liner 66 and the outer cover 64, respectively (shown in FIGS. 1 and 2). The tails 104 and 106 are generally extensions of or extending from the carrier layer 94 and are transversely discontinuous, such that when bonded to a biaxially stretchable bodyside liner 66 and/or biaxially stretchable outer cover 64, the transverse stretch of the bodyside liner 66 and/or outer cover 64 are not hindered by any lack of transverse stretchability by the material constituting the carrier layer 94.

It has been found that through the inclusion or incorporation of notches in a desired number and pattern or arrangement, absorbent core assembly components which might not otherwise provide or result in desired product stretchability or extensibility can be produced or formed to satisfy such product design capabilities. Thus, in the illustrated embodiment shown in FIG. 4, the full pad continuous layer 96 is composed of a stretch coform which has notches 108 formed on the sides and the middle. The notched absorbent core 100 can be suitably formed of a superabsorbent material meltblown with 10% pulp Pledget which has notches 110 located only along the sides thereof.

Those skilled in the art and guided by the teachings herein provided will appreciate that other suitable means or techniques to provide stretchability or extensibility to product components, such as the absorbent core assembly, can be used if desired and without departing from the practice of the invention. For example, the invention can, if desired, be practiced employing segmented absorbent materials such as disclosed in parent patent application, U.S. Ser. No. 09/698,517, filed on 27 Oct. 2000.

Figure 5:
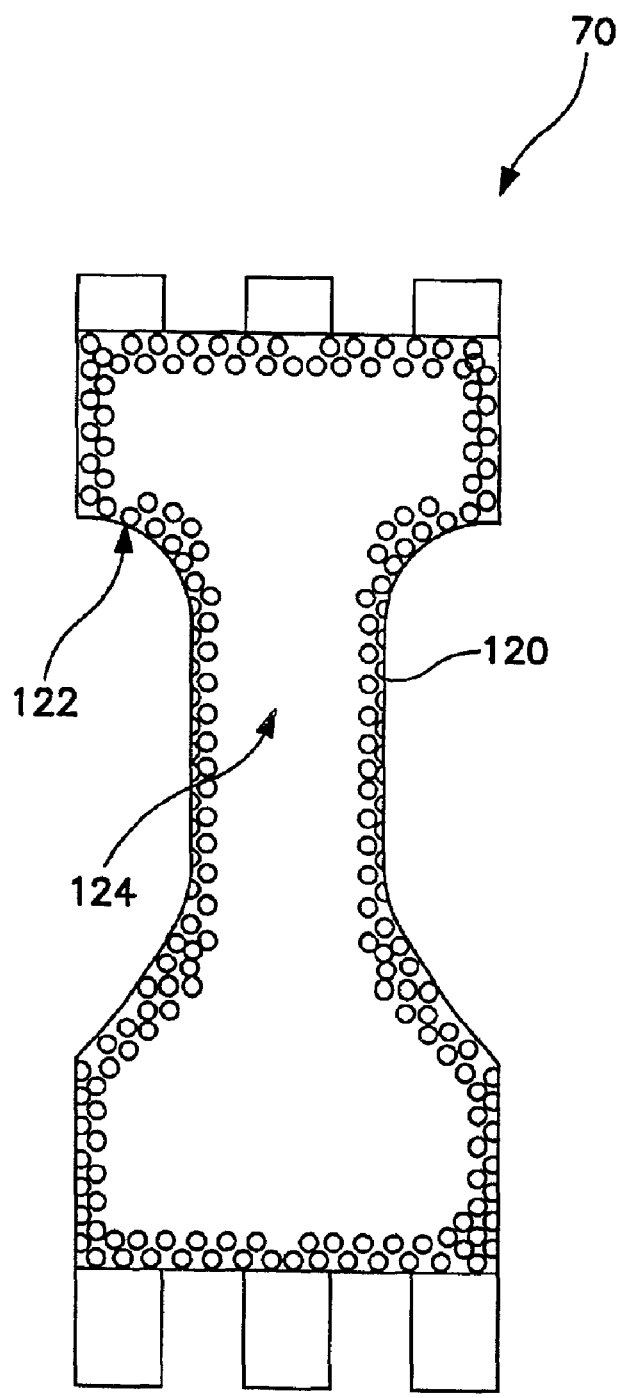
FIG. 5 is a simplified schematic plan view showing absorbent assembly seals in accordance with one preferred embodiment of the invention.

While the broader practice of the invention is not necessarily limited by the manner or means by which such components of such absorbent core assembly are fastened or otherwise joined to form the assembly, in accordance with a preferred practice of the invention it is desirable to avoid or minimize the joinder or attachments of components or elements such that the components may more freely and independently move relative to each. To that end, FIG. 5 illustrates the absorbent core assembly 70 incorporating ultra sonic point bond seals 120 about the perimeter 122 thereof, in accordance with one preferred embodiment of the invention. In accordance with a preferred practice of the invention, bonding or attachment within the interior region 124 is minimized or preferably avoided.

Point bonding is well known to those skilled in the art. Point bonding permits materials to extend or stretch between adjacent bond points and thus is a preferred bonding technique for use in the practice of the invention.

While application of such sonic bonding techniques is currently preferred, it will be appreciated that other bonding or joinder techniques can also be used. For example, bonding via an adhesive material can be used. Again, such bonding is preferably concentrated about the perimeter of the assembly and bonding or attachment within the interior region is minimized or preferably avoided. In those absorbent articles in accordance with the invention which include or rely on such adhesive bonding, an adhesive having elastic properties, such as Findley HX 2695-01 adhesive, may be used.

Individual layers or components of an absorbent article, in accordance with a preferred practice of the invention, are preferably minimally attached to other layers or components such as to increase or maximize the freedom of movement of such layers or components relative to each other.

Figure 6:
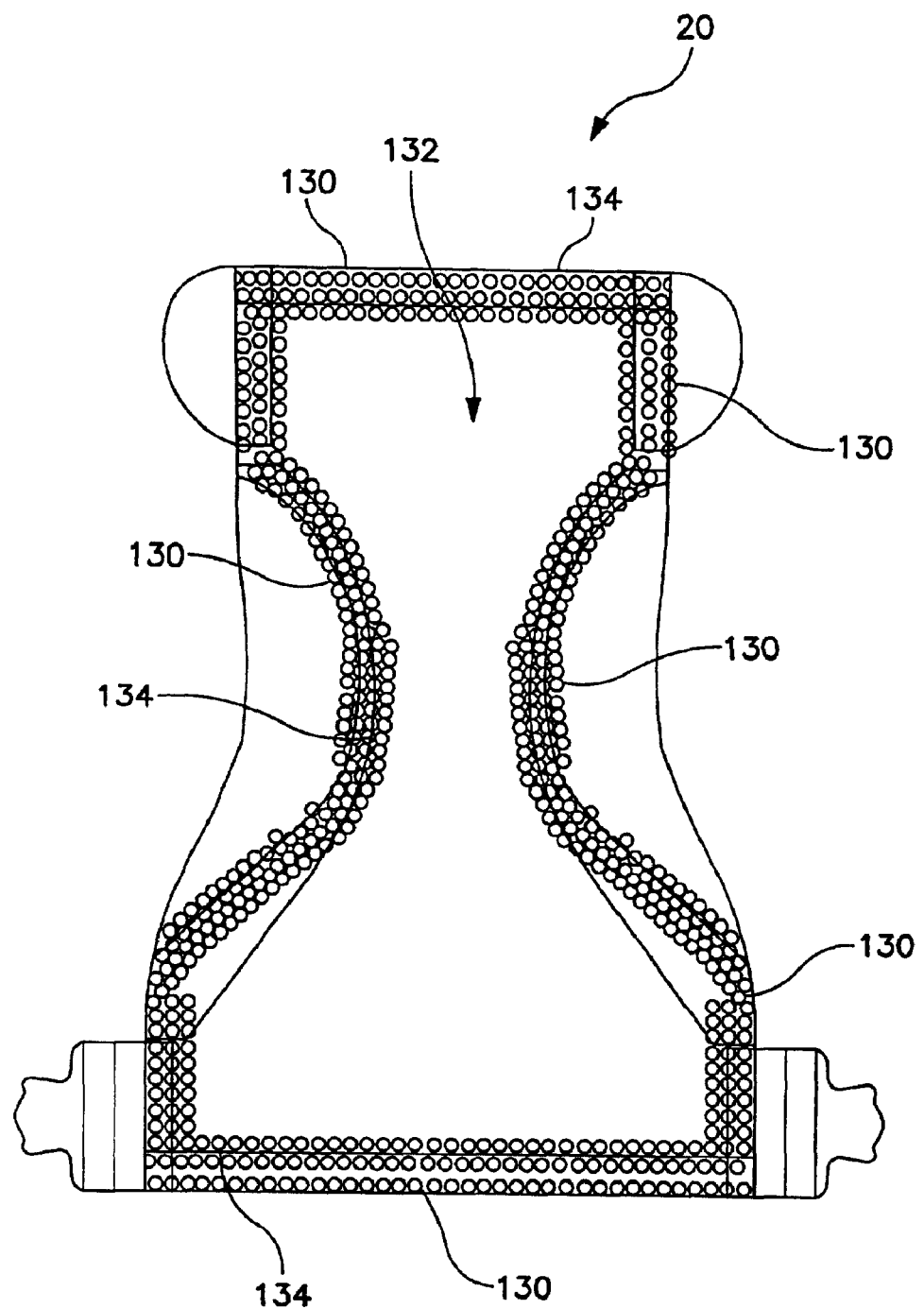
FIG. 6 is a simplified schematic plan view showing chassis perimeter seals for an absorbent garment article in accordance with one preferred embodiment of the invention.

As identified above, the outer cover 64 and the bodyside liner 66 of absorbent articles 20 in accordance with the invention are generally joined or connected in a superposed relation. FIG. 6 is a schematic plan view showing component bonding or attachment, in accordance with one preferred embodiment of the invention, in the absorbent garment article 20 described above but now simplified by not showing the containment flap members 72 and 74 in an effort to simplify illustration and facilitate comprehension. Bonding or attachment of such containment flap members is described in detail below making reference to FIG. 8.

FIG. 6 shows bonding or attachment of the components in the absorbent garment article 20 such as to desirably provide improved or increased independence of the components thereof, in accordance with one preferred embodiment of the invention. In particular, the chassis 22 includes a perimeter area 130 and an interior area 132, wherein the perimeter area 130 is defined at least in part by the cover perimeter 67 and the liner perimeter 68, described and identified above. In accordance with one preferred embodiment of the invention, the interior area 132 is desirably free of bonding. In particular, chassis components are bonded only in the perimeter area 130. As identified above, a preferred bonding technique or method is ultra sonic point bonding. FIG. 6 illustrates a plurality of ultra sonic point bond seals 134 about the chassis perimeter area 130 to bond or join the various components which comprise the absorbent article.

Thus, in accordance with one preferred embodiment of the invention and with bonding or attachment within the interior area 132 is minimized or preferably avoided. As discussed above, such point bonding desirably permits materials to extend or stretch between adjacent bond points.

Figure 7:
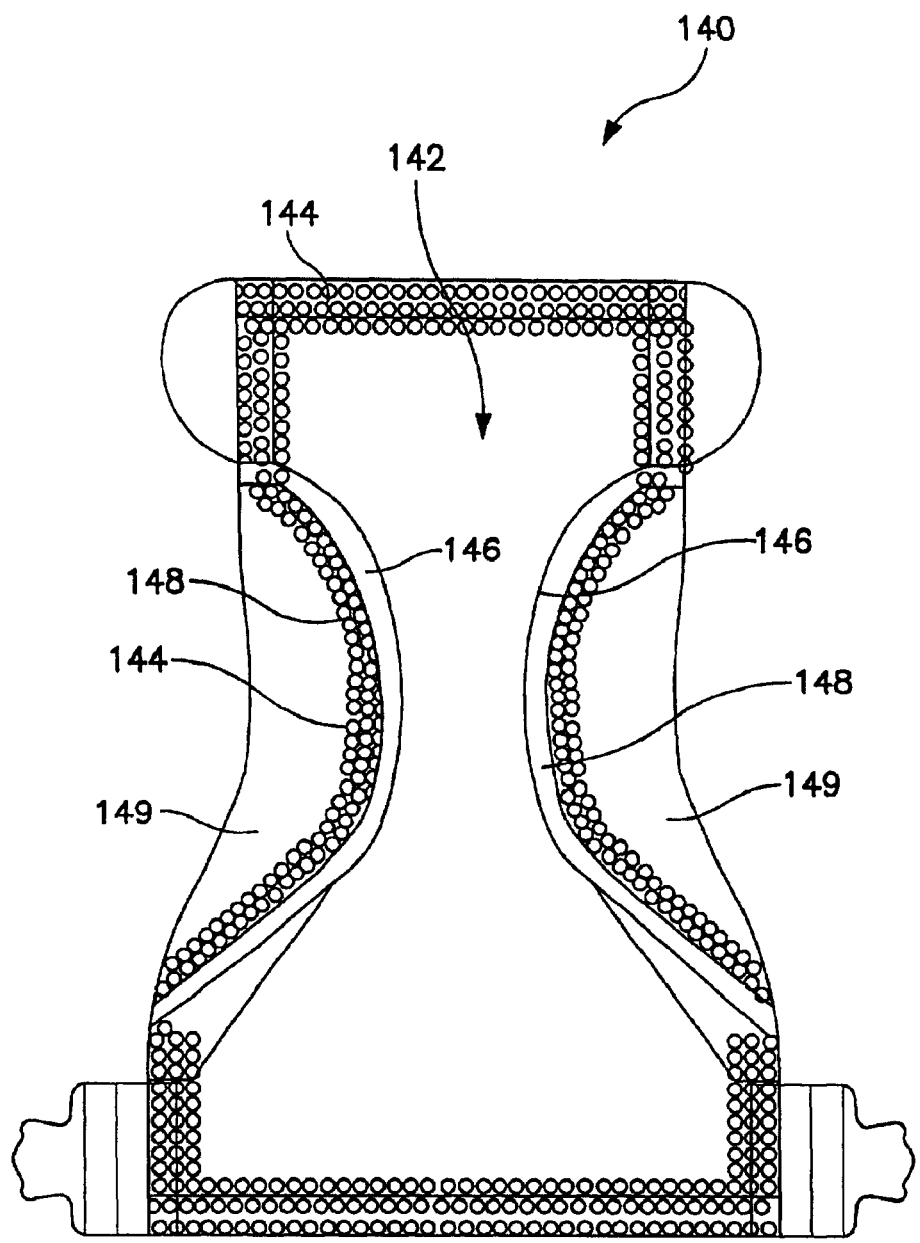
FIG. 7 is a simplified schematic plan view showing chassis perimeter seals for an absorbent garment article in accordance with another preferred embodiment of the invention.

FIG. 7 is a simplified schematic plan view showing component bonding or attachment in accordance with an alternative embodiment of the invention relative to an absorbent garment article herein designated by the reference numeral 140. The absorbent garment article 140 is generally otherwise similar to the absorbent garment article 20 described above and, as in FIG. 6, simplified by not showing the containment flap members.

In the absorbent garment article 140, the interior area 142 again preferably includes minimal bonding or attachment between components and, in accordance with a preferred embodiment, is free of bonding. Bonding or attachment by and between components in this embodiment is accomplished through a combination of ultra sonic bonds 144 and elastic adhesive bonding 146, such as discussed and described above. In particular, both the ultra sonic bonds 144 and the elastic adhesive bonding 146 occur in the perimeter area 148 of the article 140.

Similar to the absorbent core assembly attachment or bonding described above relative to FIG. 5, if the application of adhesive bonding techniques are desired or required in a particular application it is generally preferred that the adhesive have elastic properties and be used sparingly. As identified above, if adhesive bonding techniques are used or applied, the use of an adhesive having elastic properties, such as Findley HX 2695-01 adhesive, is generally preferred. Application of such adhesive might be desired in a location such as the crotch region of an article and where urine might flow between the bond points of the outer cover, liner and containment flap attachment. Extended leg cuffs 149 are also used so the outermost region of the leg cuffs 149 are not affected by the outer cover or liner.

Figure 8:
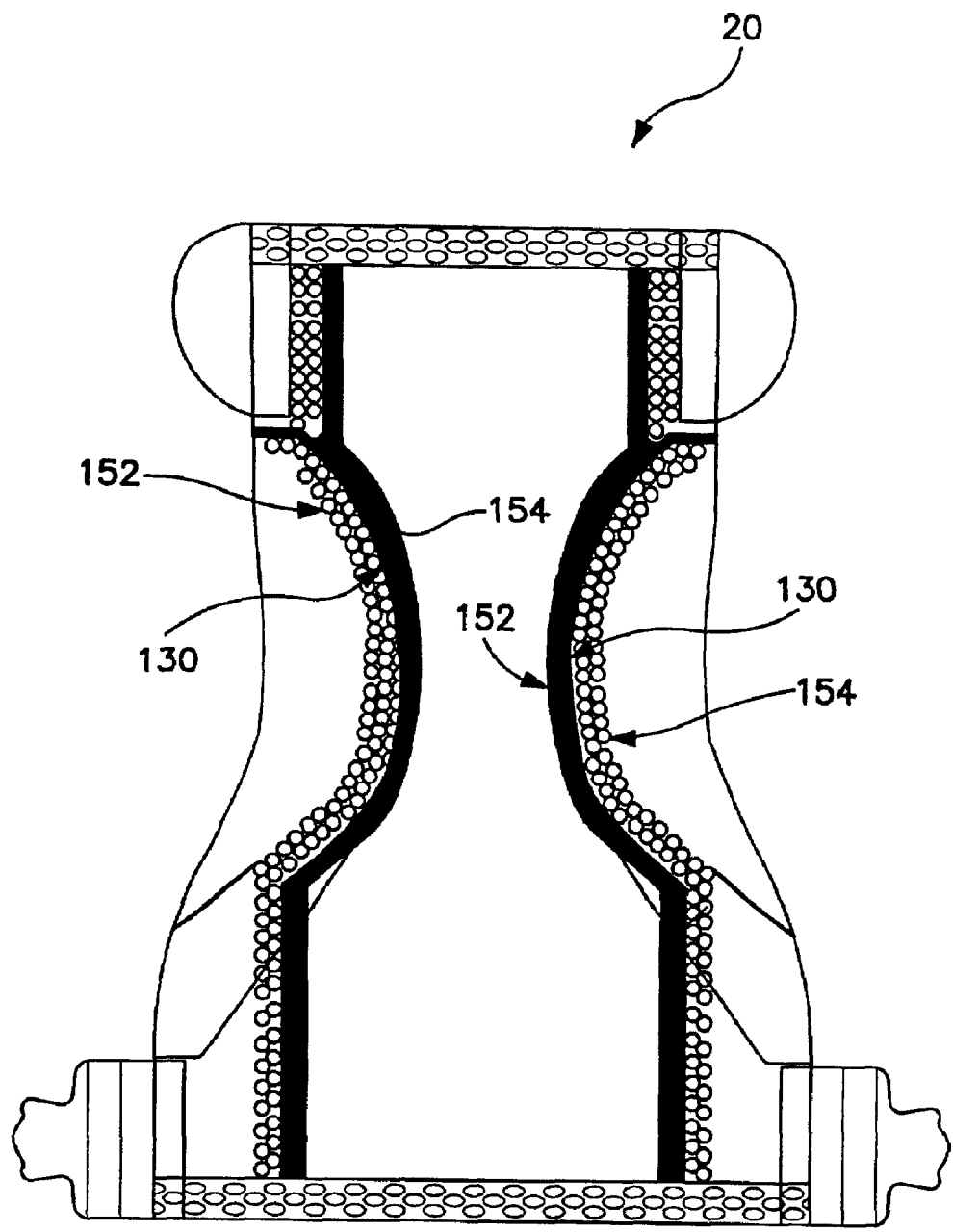
FIG. 8 is a simplified schematic plan view showing chassis perimeter seals for an absorbent garment article including containment flaps, in accordance with one embodiment of the invention.

FIG. 8 shows the absorbent garment article 20 shown in FIG. 6 but now showing bonding or attachment of the containment flap members, described above and which are not here themselves shown in an effort to simplify illustration and facilitate comprehension. In particular, the containment flap members are secured by means of a combination of ultra sonic bonds 152 and elastic adhesive bonding 154 in the article or chassis perimeter area 130.

As will be appreciated by those skilled in the art and guided by the teachings herein provided, the inclusion or use of such adhesive bonding may be desired in those embodiments wherein body exudate flow between ultra sonic bond points is of concern. Thus, application of such adhesive may be limited to the area about the sonic bond points in the crotch area of the particular absorbent garment article.

The independence of movement by or between components of the absorbent articles in accordance with this aspect of the invention can provide or result in significant product performance improvements. For example, as such an absorbent article is worn and becomes loaded with body exudate, the absorbent materials contained therewithin are pushed outward toward the outer cover. Meanwhile, the bodyside liner and containment flap members remain in close contact with the skin surface of the wearer. Skin health benefits are realized through minimizing or avoiding skin contact with the wet absorbent.

Further, whereas the components of absorbent articles have traditionally been attached, adhered or secured to each other generally over the entire areas thereof using adhesives, bonding and other techniques such as to increase the overall stiffness of the absorbent article and reduce or eliminate independence of motion therebetween, the independence of motion by or between components of the absorbent articles in accordance with this aspect of the invention can provide improved product fit and improve customer perceptions of such absorbent articles.

Those skilled in the art and guided by the teachings herein provided will appreciate that the properties of the component materials can be selectively manipulated such as to regulate or control product performance, such as to regulate and control the relative movement between components. For example, tensions and configurations can be adjusted such that the absorbent material components fill or expand downward toward the outer cover rather than upward toward the bodyside liner. Same or similar adjustments can be used to assist in maintaining the bodyside components in close contact with the wearer during walking or other leg movements. This has been demonstrated in clinical research studies, with a diaper loaded with 120 ml of synthetic urine, wherein the containment flaps and liner stayed in contact with the body, while the outer cover expanded to allow for loading and the leg cuffs created a seal. In such a study, participants included infants weighing between 16 and 28 lbs. In these tests of the study, the participants at different times each wore:

a) a commercial HUGGIES SUPREME diaper and
b) a diaper having the features of the present invention.

For each product, the diaper was applied and a photograph taken. The diaper was then loaded with 120 ml of saline solution. The children were allowed to play for approximately 45 minutes and then the diaper was rephotographed. (See also the description of FIGS. 11–25 provided herein.)

While the invention has been described above making specific reference to particular preferred embodiments wherein absorbent articles are provided which desirably self-form seals at natural body hinge points of a wearer and such can desirably provide improved or increased independence of the components thereof, those skilled in the art and guided by the teachings herein provided will appreciate that the invention can, if desired, be practiced making use of only certain or selected of the above-identified features. For example, the improved or increased independence of the components realizable through the invention can be utilized or applied in article design and manufacture without necessarily also incorporating a self-forming seal construction. Similarly, at least certain features of a self-forming seal absorbent article construction can be applied without also necessarily applying the features of improved or increased independence of article components.

In addition, at least some of the benefits associated with absorbent articles such as described above and which desirably self-form seals at natural body hinge points of a wearer and improved or increased independence of the components can be realized by certain embodiments which include leg elastic members captured between article components and such as may also desirably simplify either or both manufacture and production as well as reduce the costs associated therewith.

Figure 9:
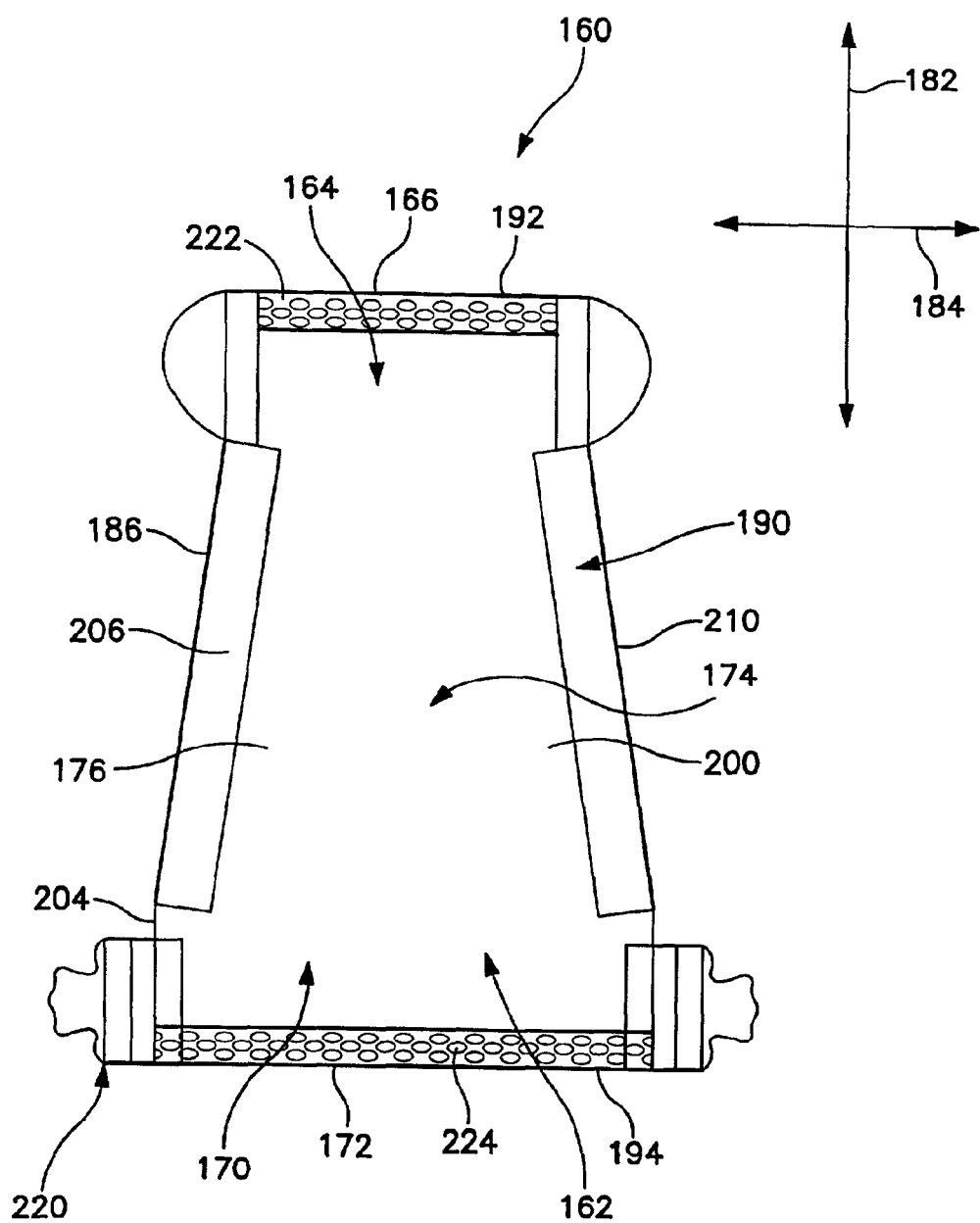
FIG. 9 is a simplified plan schematic view, similar to the view shown in FIG. 2, but now showing an absorbent garment article in accordance with another preferred embodiment of the invention.
Figure 10:
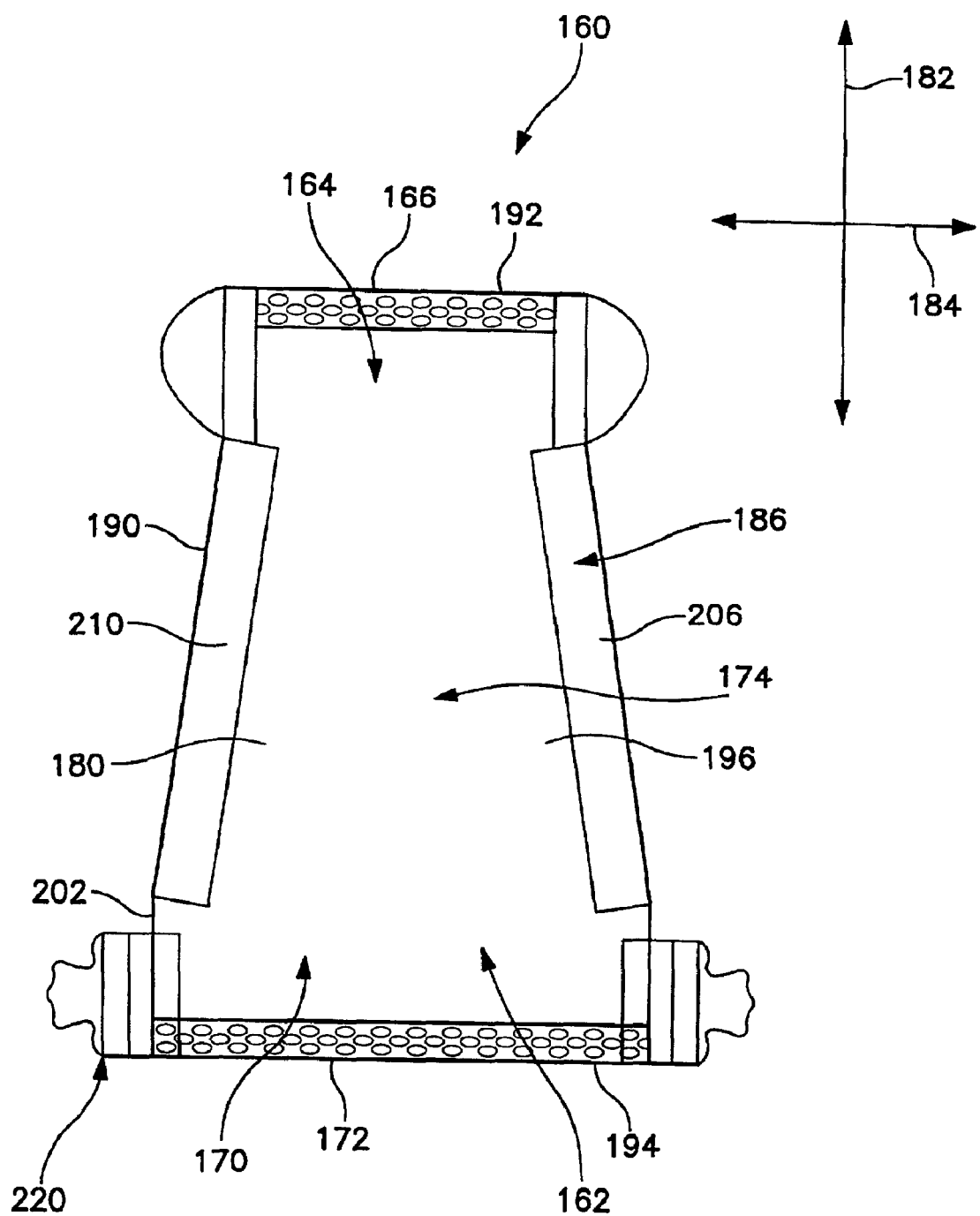
FIG. 10 is a simplified plan schematic view of the absorbent garment article shown in FIG. 9 and now showing the surface of the article that faces away from the wearer when the article is worn.

FIGS. 9 and 10 illustrate a disposable absorbent article 160 in accordance with one such preferred alternative embodiment of the invention. The absorbent article 160, similar to the absorbent article garment 20 described above, has the general form of a disposable diaper such as adapted to be worn about the lower torso by an infant. It is to be understood and appreciated, however, that such an embodiment can similarly be applied to other forms or types of absorbent articles including various disposable absorbent articles such as are generally configured to collect and contain human discharges or exudates such as, including, urine and fecal material and which articles also desirably avoid leakage of such discharge materials.

The diaper absorbent article 160 generally includes a chassis 162 and further includes or defines a front waist area 164 forming a front edge 166, a back waist area 170 forming a back edge 172, and a crotch area 174 disposed between the front and back waist areas, 164 and 170, respectively. The front waist area 164 includes the portion of the diaper 160 which, when worn, is positioned on the front of the wearer while the back waist area 170 includes the portion of the diaper 160 which, when worn, is positioned on the back of the wearer. The crotch area 174 includes that portion of the diaper 160 which, when worn, is positioned between the legs of the wearer and covers the lower torso of the wearer. The diaper absorbent article 160 forms or includes an inner surface 176 which is configured to contact the wearer, and an outer surface 180 opposite the inner surface 176 and such as configured to contact the wearer's clothing.

For ease of reference, FIGS. 9 and 10 each include arrows 182 and 184 depicting the orientation of the longitudinal and the lateral or transverse axis, respectively, for the diaper absorbent article 160. Thus, the chassis 162 has opposed longitudinal sides 186 and 190, respectively, and opposed lateral sides 192 and 194, respectively. In the diaper absorbent article 160 each of the longitudinal sides 186 and 190 and each of the lateral sides 192 and 194 is preferably straight. As will be appreciated by those skilled in the art and guided by the teachings herein provided the utilization of such a straight-sided construction will typically facilitate manufacture and minimize or reduce scrap losses as such constructions can more practically be realized and repeatedly produced, as typically desired in large scale manufacture and production.

The diaper absorbent garment article 160 and, specifically, the chassis 162 includes a biaxially extensible outer cover 196 such as serves, at least in part, to form the outer surface 180, and a biaxially extensible bodyside liner 200 such as serves, at least in part, to form the inner or wearer adjacent surface 176. The outer cover 196 forms or includes a cover perimeter 202. The bodyside liner 200 similarly forms or includes a liner perimeter 204. The outer cover 196 and the bodyside liner 200 are joined or connected, such as described in greater detail below, in a superposed relation. An absorbent core assembly, such as described above or, alternatively, such as known in the art, is interposed or otherwise located between the outer cover 196 and the bodyside liner 200.

In the illustrated embodiment, a non-curved or essentially straight leg elastic member 206 is captured between the biaxially extensible outer cover 196 and the biaxially extensible bodyside liner 200 at least along the chassis longitudinal side 186. Similarly, a non-curved or essentially straight leg elastic member 210 is captured between the biaxially extensible outer cover 196 and the biaxially extensible bodyside liner 200 at least along the chassis longitudinal side 190.

In accordance with a preferred embodiment of this aspect of the invention, either or preferably both of the leg elastic members is formed of an elastic film material such as composed of Findley HX 2695 Elastic Barrier Adhesive (EBA) and such as generally consists of a polymeric composition of white mineral oil, hydrogenated alpha-methyl styrene/styrene resin, styrene-isoprene block copolymer, and aromatic petroleum hydrocarbon resin. In particular, it will be appreciated that in such embodiments wherein the outer cover 196 and the bodyside liner 200 are each at least biaxially extensible, the capture of such non-curved or essentially straight leg elastic members therebetween desirably results in leg elastics that provide biaxial stretch without incurring the manufacturing and production complications associated with conventional curved leg elastics.

As will be appreciated, by completely enclosing such an elastic film material between the outer cover 196 and the bodyside liner 200 to provide areas of elasticity in the leg opening regions of an absorbent article, a more refined, uniform appearance can be achieved such that the absorbent article has a more pant-like form as the absorbent article desirably no longer includes leg elastic extending from the leg openings.

Further, by eliminating the layer of independent leg elastic and by eliminating the ultrasonic bonds needed to bond the elastic to the absorbent article chassis, an absorbent article in accordance with the embodiment of the invention provides better conformance to the movement and body shape of the user. The fit and comfort of the absorbent article of the invention are also improved by the more uniform distribution of force in the leg openings provided by a planar elastic material. Conventional stranded elastic present in leg elastic materials causes more localized and intense pressure on the areas of the skin of the wearer with which the elastic comes into contact. By completely enclosing an elastic film material between an outer cover and a bodyside liner to provide areas of elasticity in the leg openings of an absorbent article, a more refined, uniform appearance is achieved; the article looks more "underwear-like" as, for example, it no longer has leg elastic extending from the leg openings.

Further, the diaper absorbent garment article 160 can desirably produce, supply or otherwise results in self-forming seals, such as described herein.

The diaper absorbent garment article 160 may additionally include a fastening system 220 and waist elastics 222 and 224, as are known in the art.

In addition, from a process standpoint, the in-captured leg elastic of this embodiment of the invention provides several advantages. Conventional elastics provide machine direction stretch but not cross direction stretch. Even EBA, in its presently available form of having a facing, only achieves machine direction stretch. Consequently, current absorbent article processes require the leg elastic portion to be curved such that the leg elastic portion is curved around the chassis to reverse the stretch of the uni-directional elastic. Curving is necessary to provide machine direction stretch in the crotch portion and cross direction stretch in the upper thigh and hip portion of the absorbent article. In addition, incorporation and use of conventional extended leg elastics necessitate additional processing steps that could be eliminated by the use of the in-captured leg elastic of the invention. With extended leg elastics, the leg openings must be water-cut twice: (1) chassis is water cut to form the leg opening area between the outer cover and the bodyside liner, and (2) leg elastic material must be water cut to give desired contour. Thus, the current process has many and various challenges associated with using an extended leg elastic. For example, the extended leg elastic must be kept in place between the outer cover and bodyside liner during water cuffing; this registration between the leg elastic and the outer cover/bodyside liner is very difficult to maintain. Bonding apparatus must be properly registered to form the seam between the extended leg elastic and the outer cover/ bodyside liner combination. The additional water-cutting, registration and bonding steps of such a conventional process increase the potential for product defect. These processing steps can desirably be eliminated by using the in-captured leg elastic process of the invention.

To enhance an understanding and appreciation of the invention and the advantages and benefits attendant thereto reference will now be made to FIGS. 11, 13, 15, 17, 19 and 21–25 which depict an absorbent garment article in accordance with the embodiment of the invention here designated by the reference numeral 300, shown in FIGS. 1 and 2 and described above, and FIGS. 12, 14, 16, 18 and 20 which depict a prior art absorbent garment article, designated by the reference numeral 400.

Figure 11:
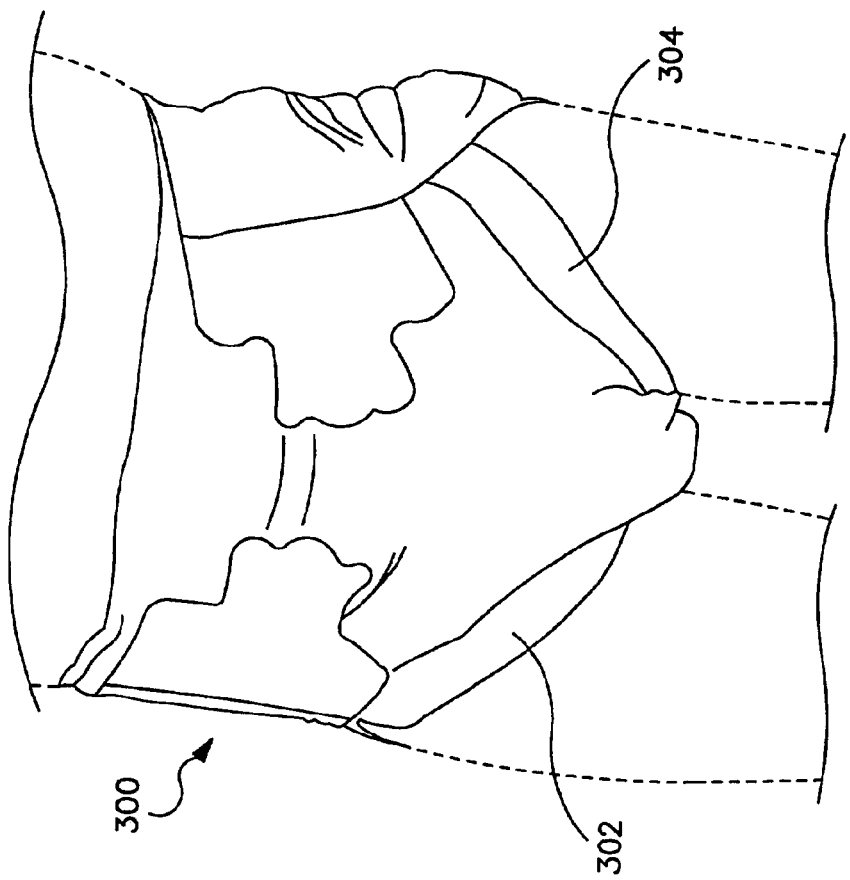
FIG. 11 is a simplified frontal perspective view of the absorbent garment article shown in FIGS. 1 and 2 as it is applied to the torso of a wearer.
Figure 13:
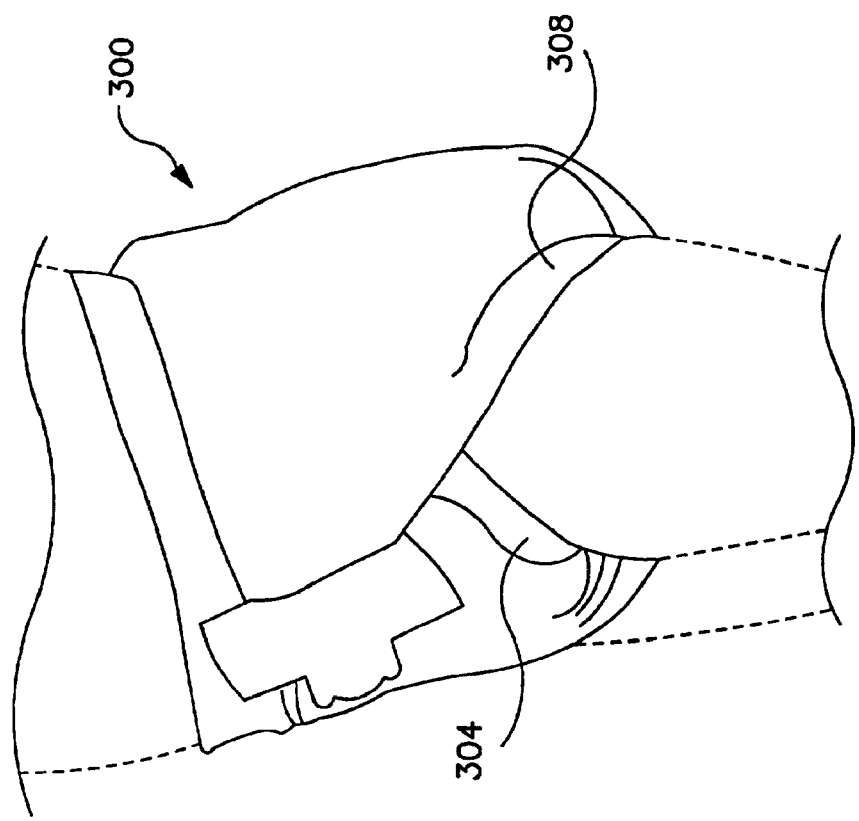
FIG. 13 is a simplified side perspective view of the absorbent garment article shown in FIG. 11 as it is applied to the torso of a wearer.
Figure 19:
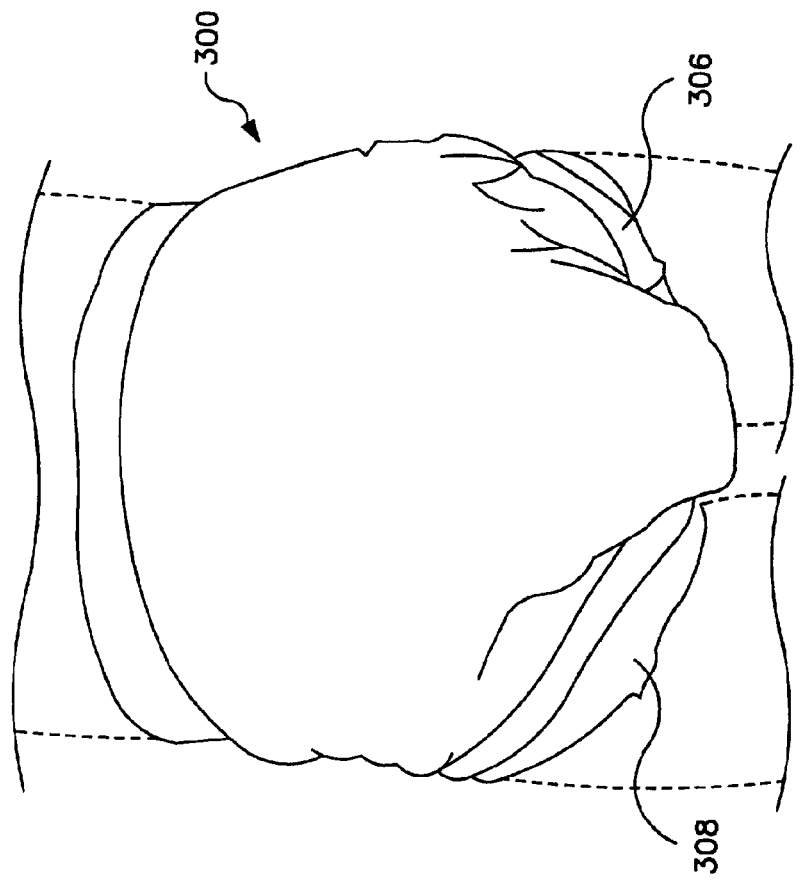
FIG. 19 is a simplified back perspective view of the absorbent garment article shown in FIG. 11 as it is applied to the torso of a wearer.
Figure 22:
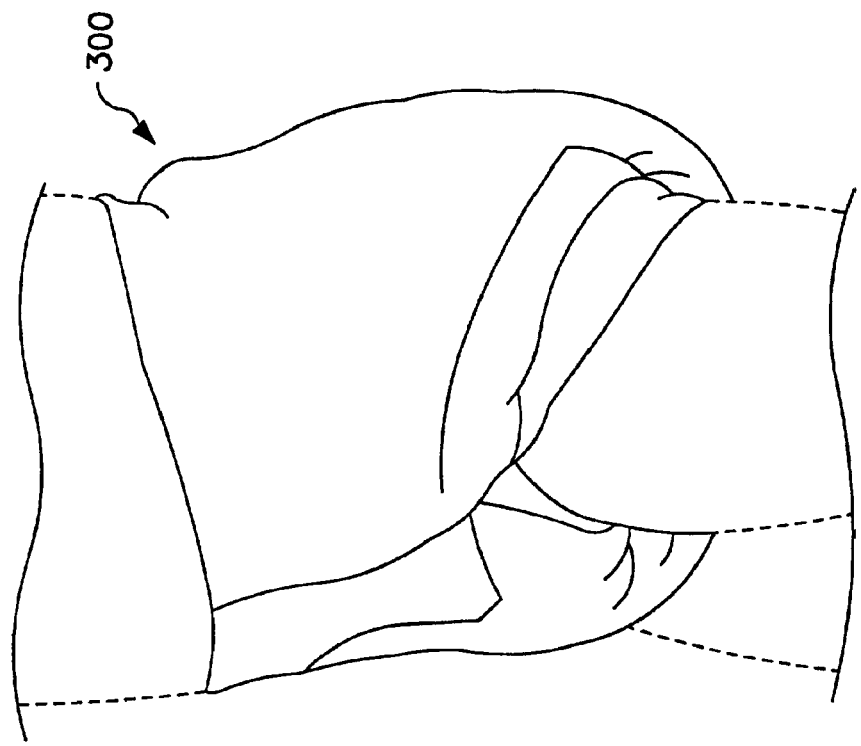
FIGS. 21–25 are simplified front, side, side showing the inner containment flap, side showing the leg seal formed thereby and back perspective view of the absorbent garment article shown in FIGS. 1 and 2 and generally corresponding to FIGS. 11, 13, 15, 17 and 19 but now showing the absorbent garment article after loading, e.g., 120 ml of liquid, and wear.
Figure 21:
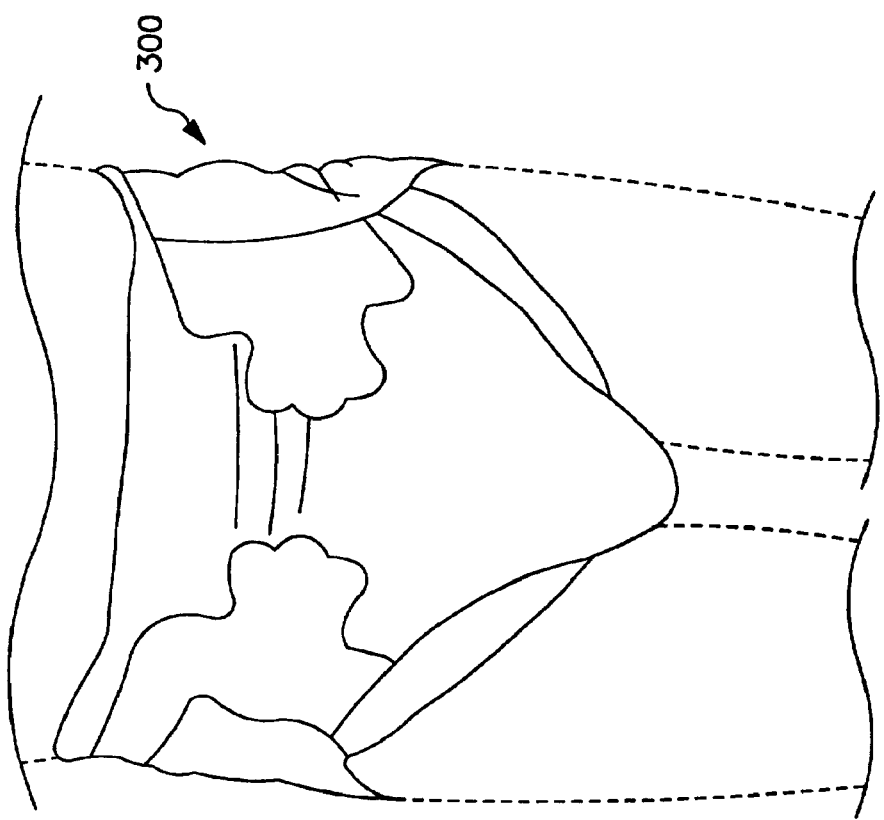
Figure 23:
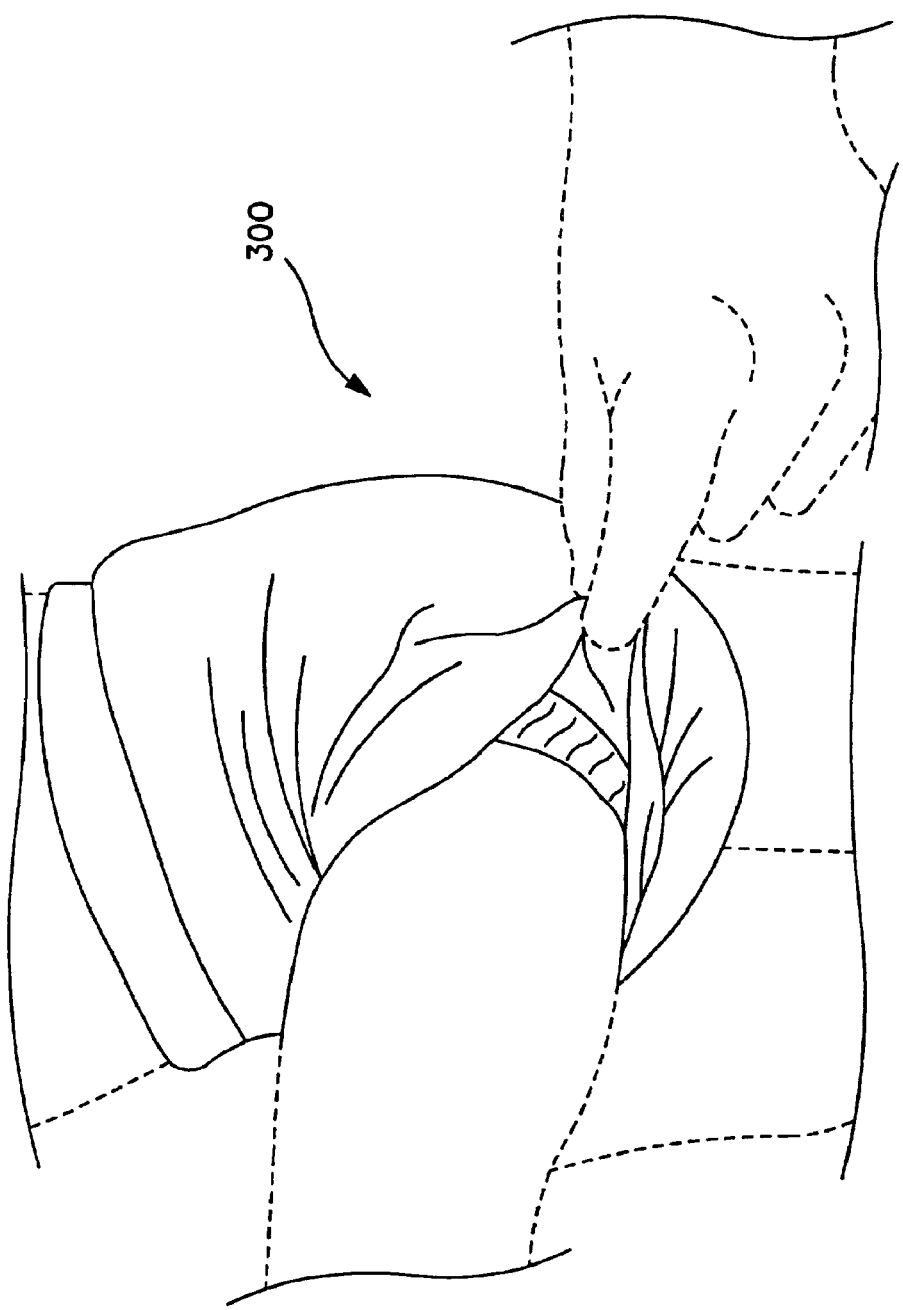
Figure 24:
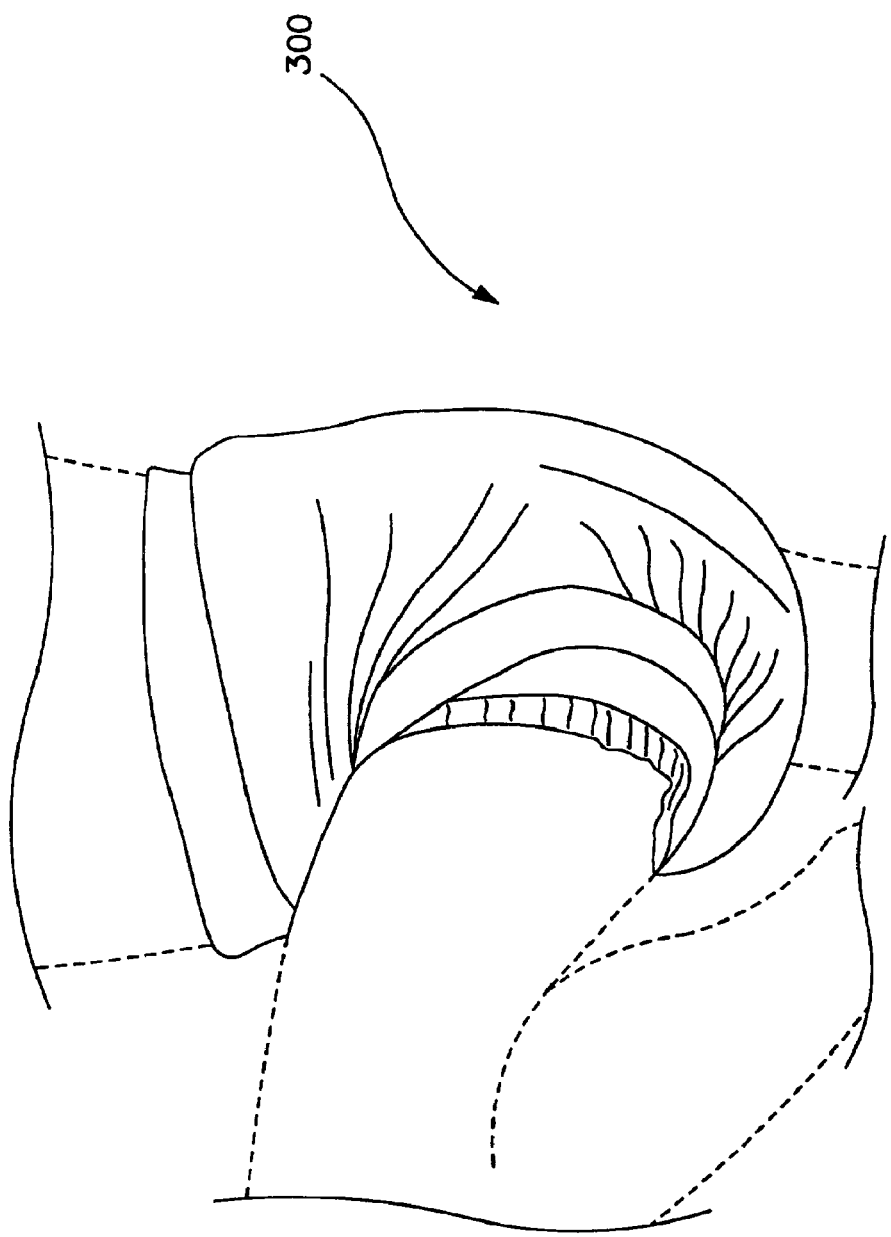
Figure 25:
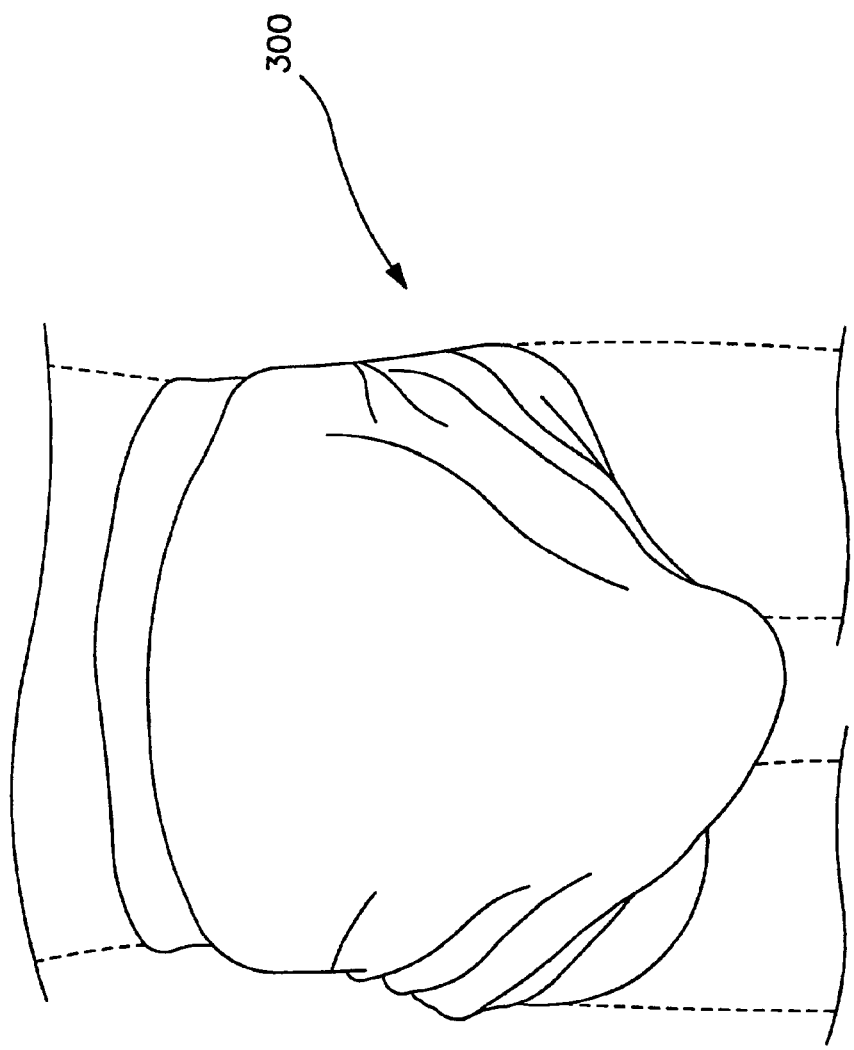

In particular, in FIGS. 11, 13 and 19, the absorbent garment article 300 is shown as including front self-forming seals, designated by the reference numerals 302 and 304, respectively, and rear self-forming seals, designated by the reference numerals 306 and 308, respectively, such as the natural hinge points of a body such as at the junction between the body torso and the leg. As shown, the absorbent garment article 300 provides a closer fit unto the skin of the wearer. Further, the absorbent garment article 300 provides a more refined, uniform pant-like appearance, such as may be desired for diaper type absorbent garment articles. That is, the absorbent garment article 300 can create a fit similar to or corresponding to that such as can normally be realized with underwear.

The improved fit, appearance and containment capabilities of the subject absorbent garment article shown in FIGS. 11, 13, 15, 17 and 19, as compared to the prior art absorbent garment article correspondingly shown in FIGS. 12, 14, 16, 18 and 20, is evident. Further, FIGS. 21–25 show that such improved fit, appearance and containment capabilities continue even after loading and wear as these figures show no appreciable change in appearance of the absorbent garment article 300 as worn on the torso even after loading and wear.

FIGS. 11–15 are drawings rendered based on the photographs taken as part of the previously described research study.

Figure 12:
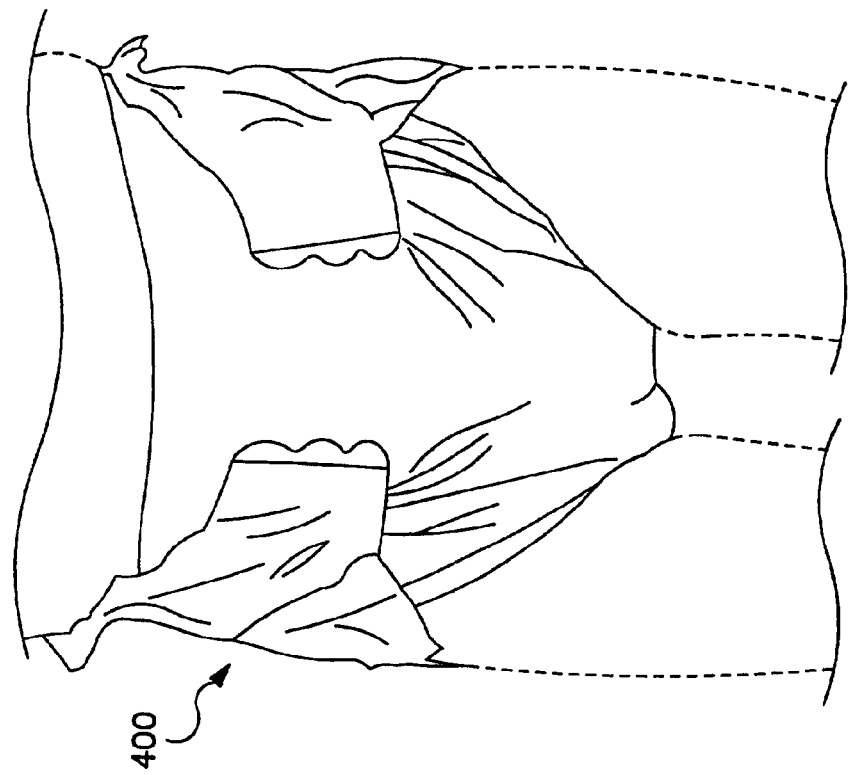
FIG. 12 is a corresponding simplified frontal perspective view of a prior art absorbent garment article which makes use of straight leg elastics as it is applied to the torso of a wearer.

In comparing the fit of the articles illustrated in FIGS. 11 and 12, the article depicted in FIG. 12 shows tension and bunching of the diaper materials. Further, tension on the diaper has caused the front waist to droop. With articles of the invention, as depicted in FIG. 11, the independence of the components allows the tension experienced by the diaper components to be dissipated and distributed throughout the whole article as opposed to just the fasteners. The construction of the articles of the invention relieves the stress experienced by the materials in use. Conventional diapers are oversized to accommodate the tension and forces experienced in use. The elastic properties of the materials used in the articles of the invention permit the tension and forces to be absorbed without compromising the fit of the article.

Figure 14:
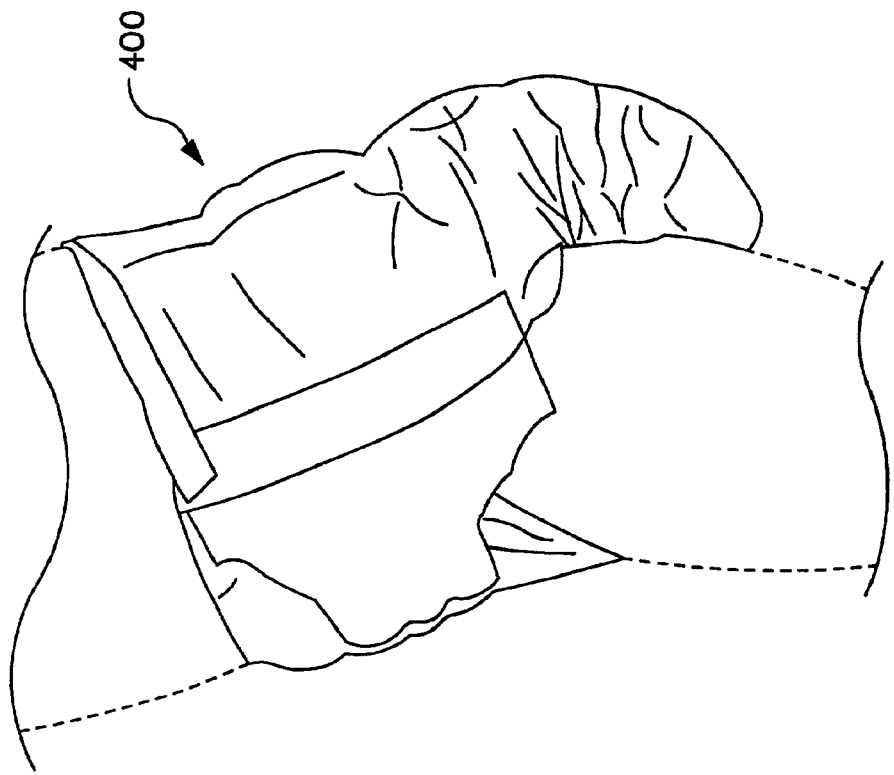
FIG. 14 is a corresponding simplified side perspective view of the prior art absorbent garment article shown in FIG. 12 as applied to the torso of a wearer.
Figure 18:
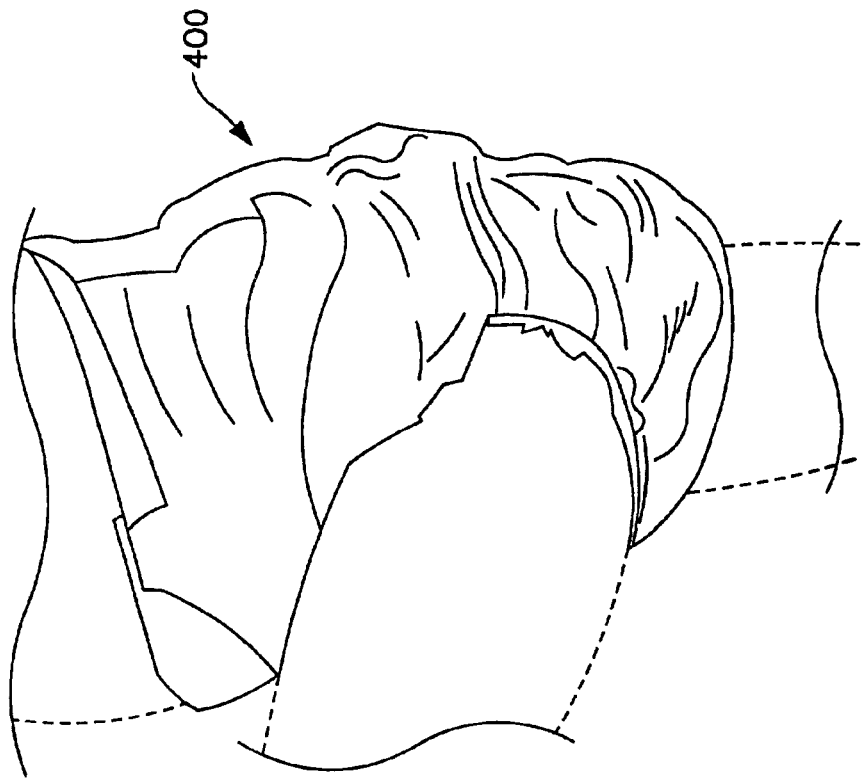
FIG. 18 is a corresponding simplified side perspective view of the prior art absorbent garment article shown in FIG. 12 as applied to the torso of a wearer and showing the leg seal formed thereby.
Figure 17:
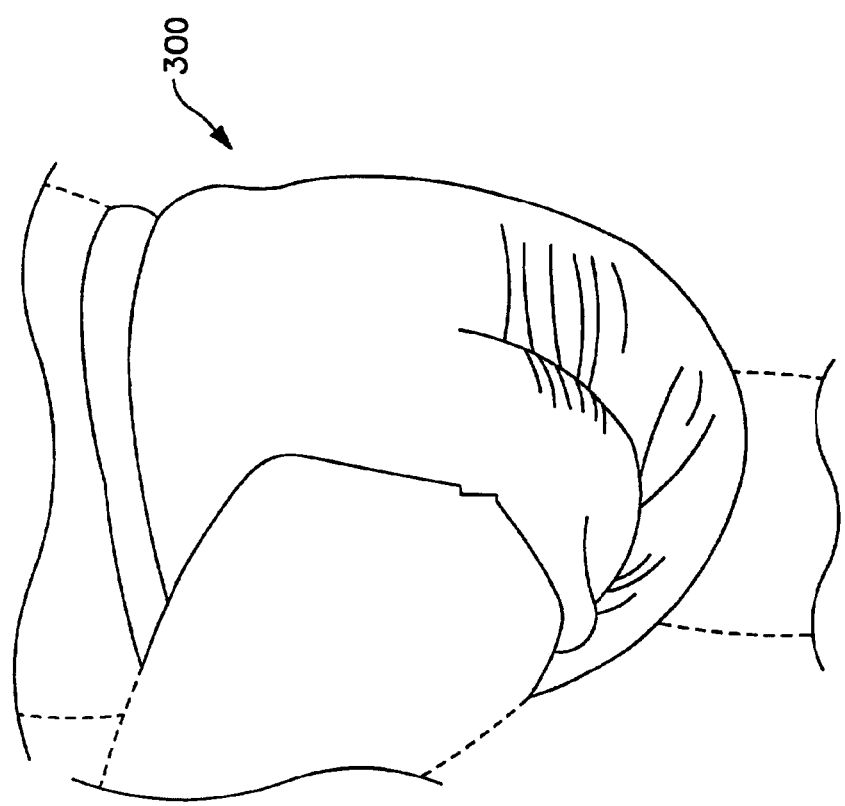
FIG. 17 is a simplified side perspective view of the absorbent garment article shown in FIG. 1 as it is applied to the torso of a wearer and showing the leg seal formed thereby.
Figure 20:
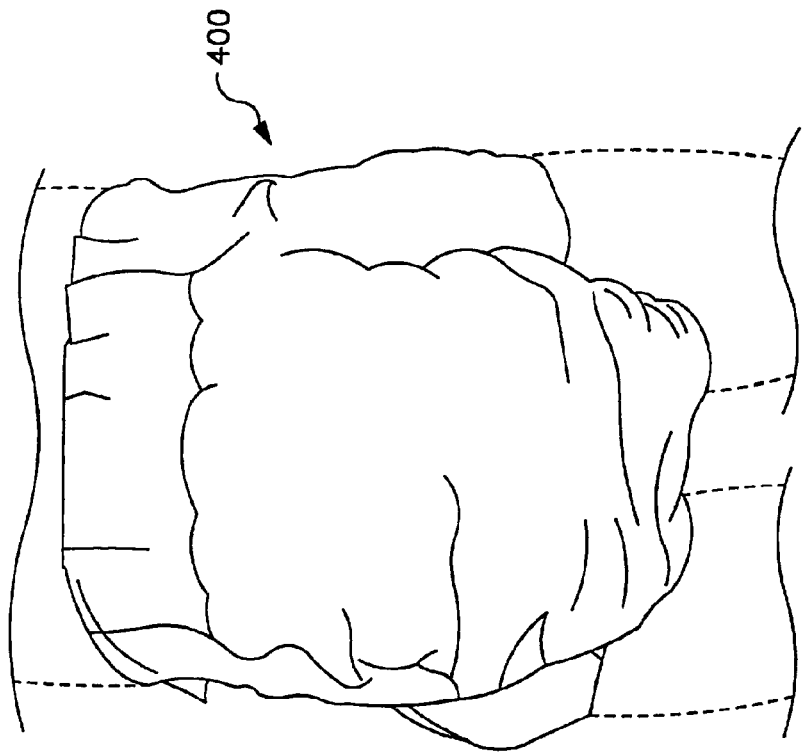
FIG. 20 is a corresponding simplified back perspective view of a prior art absorbent garment article as it is applied to the torso of a wearer.

In comparing the fit of the articles as viewed in FIGS. 13 and 14, the waist of the article in FIG. 14 is flipped over. The rear portion of the article in FIG. 14 is collapsed down and is bunched up. Further, the article in FIG. 14 has no defined leg gasket. The article of FIG. 13, representing an article of the invention, has defined seals around the leg and the waist. When the leg elastics of the articles are pulled back as illustrated in FIGS. 15 and 16, the article of the invention maintains its seal around the leg. With the conventional diaper illustrated in FIG. 16, the gasket is undefined; such as to not permit a determination of whether the material is from the containment flap or the liner. FIGS. 17 and 18 show the fit of the articles when the leg of the wearer is lifted high. The conventional diaper experiences significant bunching and the article tries to contort with the movement of the wearer. No such bunching is experienced by the article of the invention depicted in FIG. 17. The back view of an article of the invention depicted in FIG. 19 shows the self-forming seal that forms around the legs of the wearer. As previously described, FIGS. 21–25 illustrate that the fit of the articles of the invention is not negatively impacted when the article becomes loaded.

In view of the above, absorbent article configurations and constructions in accordance with the invention desirably provide improvements with respect to at least one, preferably at least two and, more preferably all three of the absorbent article qualities or properties of fit, comfort and containment capability for body fluids and exudates. As detailed below, absorbent articles, in accordance with at least certain preferred embodiments of the invention, involve the selection and use of certain specified materials in certain specific absorbent article constructions.

In accordance with at least certain aspects described above, the present invention provides an improved absorbent article which desirably self-forms seals at natural body hinge points of a wearer.

In accordance with another aspect of the invention, there is provided absorbent articles which generally desirably provide or result in improved or increased independence of the components thereof.

In accordance with yet another aspect of the invention, there is provided absorbent articles of specific construction and which include captured leg elastics such as may desirably simplify either or both manufacture and production and the costs associated therewith.

Those skilled in the art and guided by the teachings herein provided will appreciate that the self-forming seals and product advantages realized through the practice of the invention, such as improved fit, appearance and containment capabilities, for example, are believed due to one or more contributing factors such as including biaxial extensibility/stretch, diagonal extensibility/stretch, independence of components, asymmetric shape and avoidance or minimization of bonding, particularly in the interior area of the chassis, for example.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. An absorbent article adapted to be worn by a wearer, the absorbent article including a front waist area forming a front edge, a back waist area forming back edge, and a crotch area disposed between the front and back waist areas, the absorbent article comprising:

a chassis having opposed first and second longitudinal sides and opposed first and second lateral sides, the chassis having an original longitudinal length and an original lateral length, the chassis comprising components including;

an outer cover forming a cover perimeter, a bodyside liner forming a wearer adjacent surface and a liner perimeter, and an absorbent core assembly interposed between the outer cover and the bodyside liner, wherein the chassis includes a perimeter area and an interior area, wherein the perimeter area is defined at least in part by the cover perimeter and the liner perimeter, wherein the interior area comprises all area of the chassis completely surrounded by the perimeter area, and wherein bonding of the chassis is at least predominantly in the perimeter area.

2. The absorbent article of claim 1 wherein chassis components are bonded only in the perimeter area.

3. The absorbent article of claim 2 wherein the bonding of chassis components consists essentially of sonic point bonding.

4. The absorbent article of claim 2 wherein the bonding of chassis components consists essentially of elastic adhesive bonding.

5. The absorbent article of claim 1 wherein the outer cover is biaxially extensible.

6. The absorbent article of claim 1 wherein the outer cover is biaxially stretchable.

7. The absorbent article of claim 1 wherein the bodyside liner is biaxially extensible.

8. The absorbent article of claim 1 wherein the bodyside liner is biaxially stretchable.

9. The absorbent article of claim 1 additionally comprising a pair of laterally-spaced apart and longitudinally-extending containment flap members disposed along the wearer adjacent surface of the bodyside liner.

10. The absorbent article of claim 9 wherein each of the containment flap members comprises a material extensible in at least one of the longitudinal and lateral directions.

11. The absorbent article of claim 10 wherein each of the containment flap members comprises a material extensible in both the longitudinal and lateral directions.

12. The absorbent article of claim 11 wherein each of the containment flap members comprises a biaxially stretchable material.

13. The absorbent article of claim 1 additionally comprising a first extended leg cuff element disposed at the first longitudinal side and a second extended leg cuff element disposed at the second longitudinal side.

14. The absorbent article of claim 1 wherein the chassis can be longitudinally extended at least 5 percent of its original longitudinal length.

15. The absorbent article of claim 1 wherein the chassis can be longitudinally extended at least 15 percent of its original longitudinal length.

16. The absorbent article of claim 1 wherein the chassis can be longitudinally extended at least 30 percent of its original longitudinal length.

17. The absorbent article of claim 1 wherein the chassis can be longitudinally extended up to 150 percent of its original longitudinal length.

18. The absorbent article of claim 1 wherein the chassis can be longitudinally extended up to 125 percent of its original longitudinal length.

19. The absorbent article of claim 1 wherein the chassis can be longitudinally extended up to 100 percent of its original longitudinal length.

20. The absorbent article of claim 1 wherein the chassis can be laterally extended at least 10 percent of its original lateral length.

21. The absorbent article of claim 1 wherein the chassis can be laterally extended at least 25 percent of its original lateral length.

22. The absorbent article of claim 1 wherein the chassis can be laterally extended at least 50 percent of its original lateral length.

23. The absorbent article of claim 1 wherein the chassis can be laterally extended up to 200 percent of its original lateral length.

24. The absorbent article of claim 1 wherein the chassis can be laterally extended up to 150 percent of its original lateral length.

25. The absorbent article of claim 1 wherein the chassis can be laterally extended up to 125 percent of its original lateral length.

26. The absorbent article of claim 1 wherein the chassis can be diagonally extended.

27. The absorbent article of claim 26 wherein the chassis can be diagonally extended to at least 10 percent of its original diagonal length.

28. The absorbent article of claim 26 wherein the chassis can be laterally extended at least 25 percent of its original diagonal length.

29. The absorbent article of claim 26 wherein the chassis can be laterally extended at least 50 percent of its original diagonal length.

30. The absorbent article of claim 26 wherein the chassis can be laterally extended up to 200 percent of its original diagonal length.

31. The absorbent article of claim 26 wherein the chassis can be laterally extended up to 150 percent of its original diagonal length.

32. The absorbent article of claim 26 wherein the chassis can be laterally extended up to 125 percent of its original diagonal length.

33. The absorbent article of claim 1 comprising a diaper.

34. The absorbent article of claim 1 comprising a swim wear garment.

35. The absorbent article of claim 1 comprising a training pant.

36. The absorbent article of claim 1 comprising an adult incontinence garment.

37. A self-forming seal absorbent article adapted to be worn by a wearer having a body contour, the absorbent article including a front waist area forming front edge, a back waist area forming a back edge, and a crotch area disposed between the front and back waist areas, the absorbent article comprising:

a chassis having opposed first and second longitudinal sides and opposed first and second lateral sides, the chassis also providing a foot print contour adapted to match the body contour of a wearer of the absorbent article, the chassis including;

a biaxially extensible outer cover, a biaxially extensible bodyside liner forming a wearer adjacent surface, a biaxially extensible absorbent core assembly interposed between the outer cover and the bodyside liner, and a pair of laterally-spaced apart and longitudinally-extending containment flap members disposed along the wearer adjacent surface of the bodyside liner, each of the containment flap members comprises a material extensible in at least one of the longitudinal and lateral directions and wherein the chassis includes a perimeter area and an interior area, wherein the perimeter area is defined at least in part by the cover perimeter and the liner perimeter, wherein the interior area comprises all area of the chassis completely surrounded by the perimeter area, and wherein bonding of the chassis is at least predominantly in the perimeter area.

38. The self-forming seal absorbent article of claim 37 wherein the biaxially extensible outer cover comprises a polypropylene spunbond that is laminated with styrene-isoprene-styrene-based adhesive.

39. The self-forming seal absorbent article of claim 37 wherein the biaxially extensible bodyside liner comprises a surfactant-treated polypropylene spunbond, necked and creped at about 50%.

40. The self-forming seal absorbent article of claim 37 wherein each of the pair of containment flap members comprises polypropylene spunbond, necked and creped at about 50% with Elastic Barrier Adhesive.

41. A self-forming seal absorbent article adapted to be worn by a wearer having a body contour, the absorbent article including a front waist area forming a front edge, a back waist area forming a back edge, and a crotch area disposed between the front and back waist areas, the absorbent article comprising:

a biaxially stretchable chassis having opposed first and second longitudinal sides and opposed first and second lateral sides, the chassis having an original longitudinal length and an original lateral length, the chassis also providing a footprint contour adapted to match the body contour of a wearer of the absorbent article, the chassis including;

a biaxially stretchable outer cover, a biaxially stretchable bodyside liner forming a wearer adjacent surface, a biaxially stretchable absorbent core assembly interposed between the outer cover and the bodyside liner, and a pair of laterally-spaced apart and longitudinally-extending containment flap members disposed along the wearer adjacent surface of the bodyside liner, each of the containment flap members being extensible in at least one of the longitudinal and lateral directions;

wherein the chassis includes a perimeter area and an interior area, wherein the perimeter area is defined at least in part by the cover perimeter and the liner perimeter, wherein the interior area comprises all area of the chassis completely surrounded by the perimeter area, and wherein bonding of the chassis is at least predominantly in the perimeter area and wherein the chassis can be longitudinally stretched at least 5 percent and up to 150 percent of its original longitudinal length and laterally stretched at least 10 percent and up to 200 percent of its original lateral length.

42. The self-forming seal absorbent article of claim 41 wherein the chassis can be diagonally stretched at least 10 percent and up to 200 percent of its original diagonal length.

43. A disposable absorbent article adapted to be worn by a wearer, the disposable absorbent article including a front waist area forming a front edge, a back waist area forming a back edge, and a crotch area disposed between the front and back waist areas, the disposable absorbent article comprising:

a chassis having opposed first and second longitudinal sides and opposed first and second lateral sides, the chassis having an original longitudinal length and an original lateral length, the chassis comprising components including;

an outer cover forming a cover perimeter, a bodyside liner forming a wearer adjacent surface and a liner perimeter, and an absorbent core assembly interposed between the outer cover and the bodyside liner, the chassis including a perimeter area, defined at least in part by the cover perimeter and the liner perimeter, and an interior area comprising all area of the chassis completely surrounded by the perimeter area, wherein the outer cover and the bodyside liner are joined together about the chassis perimeter area in a superposed relation and wherein the entire chassis interior area is free of bonding.

44. The absorbent article of claim 1 wherein the entire chassis interior area is free of bonding.

45. The absorbent article of claim 37 wherein the entire chassis interior area is free of bonding.

* * * * *